United States Patent
Jackowski et al.

(10) Patent No.: US 10,525,601 B2
(45) Date of Patent: Jan. 7, 2020

(54) MOTOR AND CONTROLLER INTEGRATION FOR A LEGGED ROBOT

(71) Applicant: Boston Dynamics, Inc., Waltham, MA (US)

(72) Inventors: Zachary John Jackowski, Sommerville, MA (US); Kyle Rogers, Carlisle, MA (US); Adam Young, Waltham, MA (US)

(73) Assignee: Boston Dynamics, Inc., Waltham, MA (US)

( * ) Notice: Subject to any disclaimer, the term of this patent is extended or adjusted under 35 U.S.C. 154(b) by 0 days.

(21) Appl. No.: 16/391,964

(22) Filed: Apr. 23, 2019

(65) Prior Publication Data

US 2019/0248021 A1    Aug. 15, 2019

Related U.S. Application Data

(63) Continuation of application No. 15/380,593, filed on Dec. 15, 2016, now Pat. No. 10,300,609.

(51) Int. Cl.
*B25J 13/08* (2006.01)
*B25J 18/04* (2006.01)
(Continued)

(52) U.S. Cl.
CPC ........... *B25J 13/088* (2013.01); *A61F 5/0125* (2013.01); *B25J 9/12* (2013.01); *B25J 18/04* (2013.01); *H02K 7/003* (2013.01); *H02K 9/06* (2013.01); *H02K 9/22* (2013.01); *H02K 11/215* (2016.01); *H02K 11/24* (2016.01); *H02K 11/25* (2016.01);
(Continued)

(58) Field of Classification Search
CPC .. B25J 13/088; B25J 9/12; B25J 18/04; A61F 5/0125; H02K 11/215; H02K 11/24; H02K 11/25; H02K 11/33; H02K 7/003; H02K 7/116; H02K 2211/03; H02K 9/06; H02K 9/22
See application file for complete search history.

(56) References Cited

U.S. PATENT DOCUMENTS 5,006,744 A    4/1991    Archer et al.
5,912,541 A    6/1999    Bigler et al.
(Continued)

FOREIGN PATENT DOCUMENTS

| JP | 2014075866 A | 4/2014 |
| WO | 2015122069 A1 | 8/2015 |
| WO | 2016158978 A1 | 10/2016 |

OTHER PUBLICATIONS

International Search Report, Application No. PCT/US2017/066174, dated Oct. 30, 2018, 9 pages.

*Primary Examiner* — Emily P Pham
(74) *Attorney, Agent, or Firm* — Honigman LLP

(57) ABSTRACT

An example robot includes: a motor disposed within a housing at a joint configured to control motion of a member of a robot; a controller including one or more printed circuit boards (PCBs) disposed within the housing and including a plurality of field-effect transistors (FETs) disposed on a surface of a PCB of the one or more PCBs facing the motor; a rotary position sensor mounted on the controller; a shaft coupled to a rotor of the motor and extending therefrom to the controller; and a magnet mounted within the shaft at an end of the shaft facing the controller.

23 Claims, 23 Drawing Sheets

(51) Int. Cl.
  *A61F 5/01* (2006.01)
  *H02K 7/00* (2006.01)
  *H02K 9/22* (2006.01)
  *H02K 11/215* (2016.01)
  *H02K 11/24* (2016.01)
  *H02K 11/25* (2016.01)
  *H02K 11/33* (2016.01)
  *B25J 9/12* (2006.01)
  *H02K 9/06* (2006.01)
  *H02K 7/116* (2006.01)

(52) U.S. Cl.
  CPC .............. *H02K 11/33* (2016.01); *H02K 7/116* (2013.01); *H02K 2211/03* (2013.01)

(56) References Cited

U.S. PATENT DOCUMENTS

| | | | |
|---|---|---|---|
| 6,258,007 B1 | 7/2001 | Kristjansson | |
| 7,352,092 B2 | 4/2008 | Levine et al. | |
| 8,004,135 B2 | 8/2011 | Peterson et al. | |
| 8,913,748 B2 | 12/2014 | Ho et al. | |
| 9,211,640 B2 | 12/2015 | Sato et al. | |
| 9,687,377 B2 | 6/2017 | Han et al. | |
| 2006/0071622 A1 | 4/2006 | Townsend et al. | |
| 2008/0217437 A1 | 9/2008 | Vanden Berghe et al. | |
| 2011/0067517 A1* | 3/2011 | Ihrke | B25J 9/126 74/490.03 |
| 2011/0314935 A1 | 12/2011 | Krippner et al. | |
| 2012/0010749 A1* | 1/2012 | van der Merwe | A61F 2/54 700/264 |
| 2012/0283845 A1* | 11/2012 | Herr | A61F 2/66 623/24 |
| 2014/0326530 A1 | 11/2014 | Asao et al. | |
| 2015/0068350 A1* | 3/2015 | Kirihara | B25J 17/02 74/490.05 |
| 2015/0134079 A1* | 5/2015 | Yoon | A61F 2/68 623/27 |
| 2015/0257903 A1* | 9/2015 | Perry | A61F 2/70 623/24 |
| 2016/0128890 A1* | 5/2016 | LaChappelle | A61H 3/00 623/30 |
| 2016/0192535 A1 | 6/2016 | Yamanaka | |
| 2016/0221197 A1 | 8/2016 | Claffee et al. | |
| 2017/0008554 A1 | 1/2017 | Hirotani et al. | |
| 2018/0194003 A1 | 7/2018 | Jackson et al. | |
| 2019/0001501 A1 | 1/2019 | Roberts | |

* cited by examiner

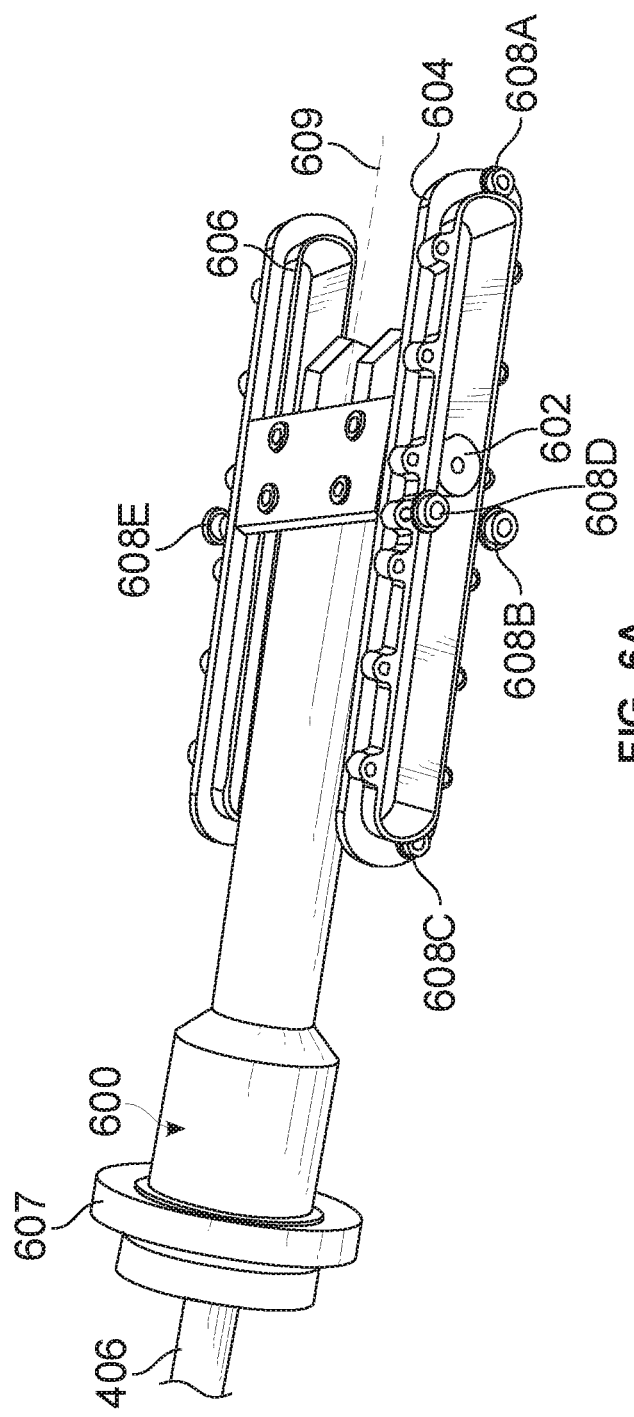
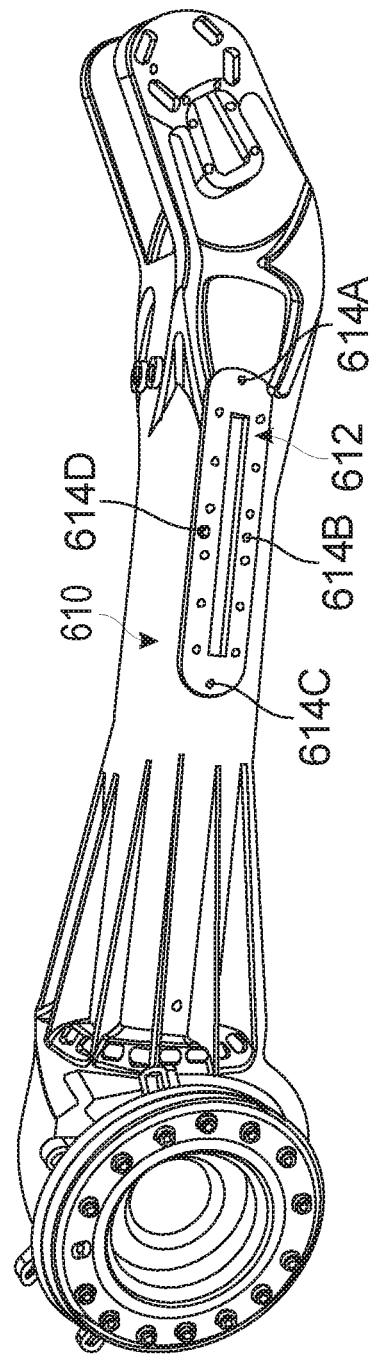
FIG. 6A
FIG. 6B

MOTOR AND CONTROLLER INTEGRATION FOR A LEGGED ROBOT

CROSS REFERENCE TO RELATED APPLICATIONS

This U.S. patent application is a continuation of, and claims priority under 35 U.S.C. § 120 from, U.S. patent application Ser. No. 15/380,593, filed on Dec. 15, 2016. The disclosure of this prior application is considered part of the disclosure of this application and is hereby incorporated by reference in its entirety.

BACKGROUND

An example robot may have a plurality of members forming the robot's legs and arms. The motion of these members may be controlled by actuators such as hydraulic cylinders and motors. The robot may also include a controller configured to control operation of the various actuators based on inputs from various sensors coupled to the robot. The amount of components and sensors of the robot in addition to the extent of wires and connections made throughout the robot affect its reliability.

SUMMARY

The present disclosure describes implementations that relate to motor and controller integration for a legged robot. In a first example implementation, the present disclosure describes a robot. The robot includes: (i) a motor disposed within a housing and at a joint, wherein the joint is configured to control motion of a member of the robot; (ii) a power stage printed circuit board (PCB) disposed within the housing and including a plurality of field-effect transistors (FETs) disposed on a first surface of the power stage PCB facing the motor; (iii) a logic stage PCB including (a) one or more processors in communication with the power stage PCB, and (b) a rotary position sensor mounted on a surface of the logic stage PCB, wherein the surface of the logic stage PCB faces a second surface of the power stage PCB opposite the first surface, wherein the power stage PCB is disposed between the motor and the logic stage PCB, and wherein the power stage PCB and logic stage PCB are arranged on respective axially spaced planes; (iv) a shaft coupled to a rotor of the motor and configured to extend through the power stage PCB; and (v) a magnet mounted at an end of the shaft facing the rotary position sensor.

In a second example implementation, the present disclosure describes an assembly. The assembly includes: (i) a motor disposed within a housing and at a joint, wherein the joint is configured to control motion of a member of a robot; (ii) a controller including (a) one or more printed circuit boards (PCBs) disposed within the housing, and (b) a plurality of field-effect transistors (FETs) disposed on a surface of a PCB of the one or more PCBs, wherein the FETs face the motor; (iii) a rotary position sensor mounted on the controller; (iv) a shaft coupled to a rotor of the motor and extending therefrom to the controller; and (iv) a magnet mounted within the shaft at an end of the shaft facing the controller.

The foregoing summary is illustrative only and is not intended to be in any way limiting. In addition to the illustrative aspects, implementations, and features described above, further aspects, implementations, and features will become apparent by reference to the figures and the following detailed description.

DESCRIPTION OF DRAWINGS

FIG. 6A illustrates a carrier having rollers coupled thereto, in accordance with an example implementation.

FIG. 6B illustrates an upper leg member configured to receive a carrier and rails therein, in accordance with an example implementation.

DETAILED DESCRIPTION

The following detailed description describes various features and operations of the disclosed systems with reference to the accompanying figures. The illustrative implementations described herein are not meant to be limiting. Certain aspects of the disclosed systems can be arranged and combined in a wide variety of different configurations, all of which are contemplated herein.

Further, unless context suggests otherwise, the features illustrated in each of the figures may be used in combination with one another. Thus, the figures should be generally viewed as component aspects of one or more overall implementations, with the understanding that not all illustrated features are necessary for each implementation.

Additionally, any enumeration of elements, blocks, or steps in this specification or the claims is for purposes of clarity. Thus, such enumeration should not be interpreted to require or imply that these elements, blocks, or steps adhere to a particular arrangement or are carried out in a particular order.

By the term "substantially" it is meant that the recited characteristic, parameter, or value need not be achieved exactly, but that deviations or variations, including for example, tolerances, measurement error, measurement accuracy limitations and other factors known to skill in the art, may occur in amounts that do not preclude the effect the characteristic was intended to provide.

I. EXAMPLE ROBOTIC SYSTEMS

Figure 1:
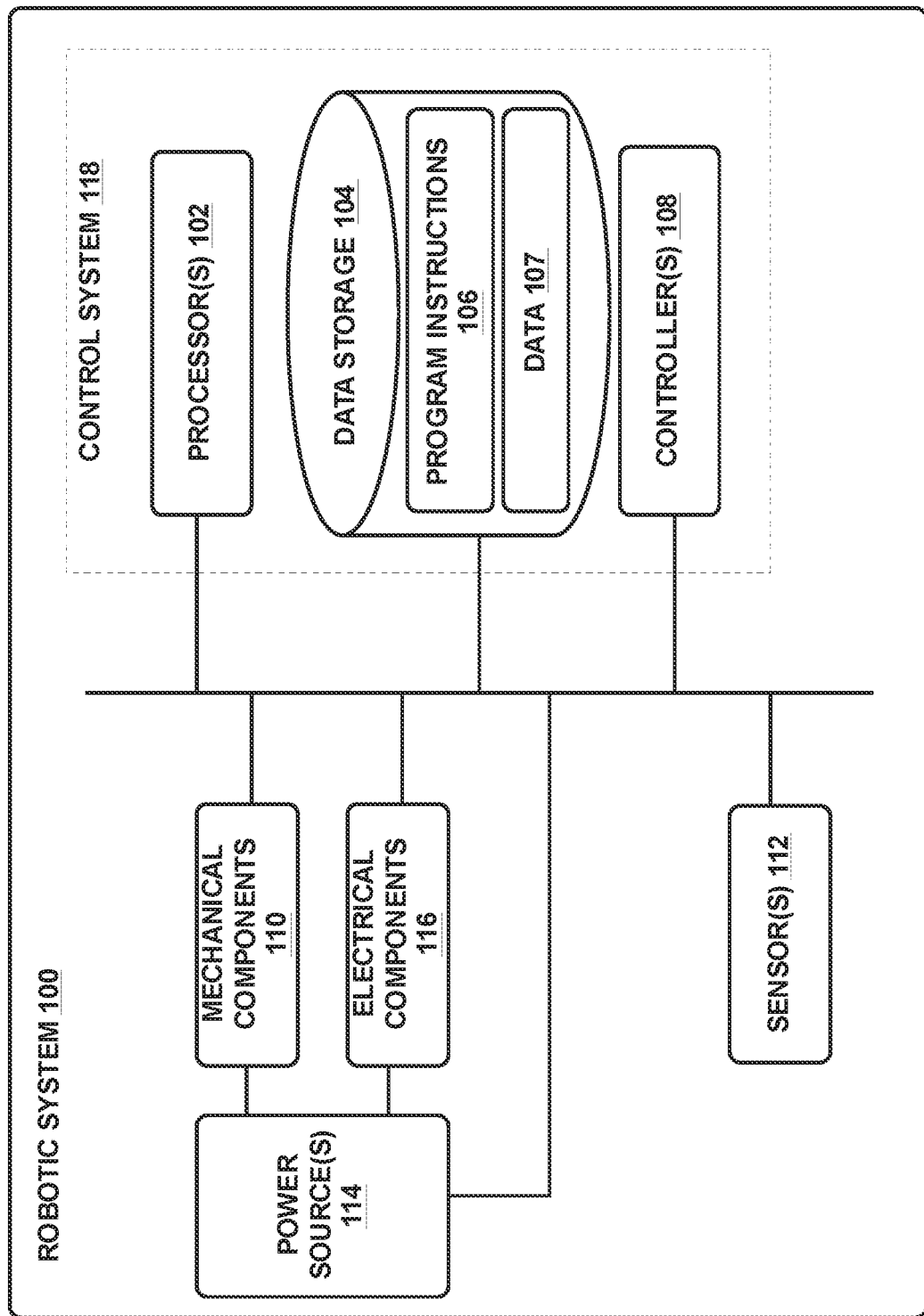
FIG. 1 illustrates a configuration of a robotic system, in accordance with an example implementation.

FIG. 1 illustrates an example configuration of a robotic system that may be used in connection with the implementations described herein. The robotic system 100 may be configured to operate autonomously, semi-autonomously, and/or using directions provided by user(s). The robotic system 100 may be implemented in various forms, such as a biped robot, quadruped robot, or some other arrangement. Furthermore, the robotic system 100 may also be referred to as a robot, robotic device, or mobile robot, among other designations, and could be part of an exoskeleton or human assisting device.

As shown in FIG. 1, the robotic system 100 may include processor(s) 102, data storage 104, and controller(s) 108, which together may be part of a control system 118. The robotic system 100 may also include sensor(s) 112, power source(s) 114, mechanical components 110, and electrical components 116. Nonetheless, the robotic system 100 is shown for illustrative purposes, and may include more or fewer components. The various components of robotic system 100 may be connected in any manner, including wired or wireless connections. Further, in some examples, components of the robotic system 100 may be distributed among multiple physical entities rather than a single physical entity. Other example illustrations of robotic system 100 may exist as well.

Processor(s) 102 may operate as one or more general-purpose hardware processors or special purpose hardware processors (e.g., digital signal processors, application specific integrated circuits, etc.). The processor(s) 102 may be configured to execute computer-readable program instructions 106, and manipulate data 107, both of which are stored in the data storage 104. The processor(s) 102 may also directly or indirectly interact with other components of the robotic system 100, such as sensor(s) 112, power source(s) 114, mechanical components 110, and/or electrical components 116.

The data storage 104 may be one or more types of hardware memory. For example, the data storage 104 may include or take the form of one or more computer-readable storage media that can be read or accessed by processor(s) 102. The one or more computer-readable storage media can include volatile and/or non-volatile storage components, such as optical, magnetic, organic, or another type of memory or storage, which can be integrated in whole or in part with processor(s) 102. In some implementations, the data storage 104 can be a single physical device. In other implementations, the data storage 104 can be implemented using two or more physical devices, which may communicate with one another via wired or wireless communication. As noted previously, the data storage 104 may include the computer-readable program instructions 106 and the data 107. The data 107 may be any type of data, such as configuration data, sensor data, and/or diagnostic data, among other possibilities.

The controller 108 may include one or more electrical circuits, units of digital logic, computer chips, and/or microprocessors that are configured to (perhaps among other tasks), interface between any combination of the mechanical components 110, the sensor(s) 112, the power source(s) 114, the electrical components 116, the control system 118, and/or a user of the robotic system 100. In some implementations, the controller 108 may be a purpose-built embedded device for performing specific operations with one or more subsystems of the robotic system 100.

The control system 118 may monitor and physically change the operating conditions of the robotic system 100. In doing so, the control system 118 may serve as a link between portions of the robotic system 100, such as between mechanical components 110 and/or electrical components 116. In some instances, the control system 118 may serve as an interface between the robotic system 100 and another computing device. Further, the control system 118 may serve as an interface between the robotic system 100 and a user. The instance, the control system 118 may include various components for communicating with the robotic system 100, including a joystick, buttons, and/or ports, etc. The example interfaces and communications noted above may be implemented via a wired or wireless connection, or both. The control system 118 may perform other operations for the robotic system 100 as well.

During operation, the control system 118 may communicate with other systems of the robotic system 100 via wired or wireless connections, and may further be configured to communicate with one or more users of the robot. As one possible illustration, the control system 118 may receive an input (e.g., from a user or from another robot) indicating an instruction to perform a particular gait in a particular direction, and at a particular speed. A gait is a pattern of movement of the limbs of an animal, robot, or other mechanical structure.

Based on this input, the control system 118 may perform operations to cause the robotic system 100 to move according to the requested gait. As another illustration, a control system may receive an input indicating an instruction to move to a particular geographical location. In response, the control system 118 (perhaps with the assistance of other components or systems) may determine a direction, speed, and/or gait based on the environment through which the robotic system 100 is moving en route to the geographical location.

Operations of the control system 118 may be carried out by the processor(s) 102. Alternatively, these operations may be carried out by the controller 108, or a combination of the processor(s) 102 and the controller 108. In some implementations, the control system 118 may partially or wholly reside on a device other than the robotic system 100, and therefore may at least in part control the robotic system 100 remotely.

Mechanical components 110 represent hardware of the robotic system 100 that may enable the robotic system 100 to perform physical operations. As a few examples, the robotic system 100 may include physical members such as leg(s), arm(s), and/or wheel(s). The physical members or other parts of robotic system 100 may further include actuators arranged to move the physical members in relation to one another. The robotic system 100 may also include one or more structured bodies for housing the control system 118 and/or other components, and may further include other types of mechanical components. The particular mechanical components 110 used in a given robot may vary based on the design of the robot, and may also be based on the operations and/or tasks the robot may be configured to perform.

In some examples, the mechanical components 110 may include one or more removable components. The robotic system 100 may be configured to add and/or remove such removable components, which may involve assistance from a user and/or another robot. For example, the robotic system 100 may be configured with removable arms, hands, feet, and/or legs, so that these appendages can be replaced or changed as needed or desired. In some implementations, the robotic system 100 may include one or more removable and/or replaceable battery units or sensors. Other types of removable components may be included within some implementations.

The robotic system 100 may include sensor(s) 112 arranged to sense aspects of the robotic system 100. The sensor(s) 112 may include one or more force sensors, torque sensors, velocity sensors, acceleration sensors, position sensors, proximity sensors, motion sensors, location sensors, load sensors, temperature sensors, touch sensors, depth sensors, ultrasonic range sensors, infrared sensors, object sensors, and/or cameras, among other possibilities. Within some examples, the robotic system 100 may be configured to receive sensor data from sensors that are physically separated from the robot (e.g., sensors that are positioned on other robots or located within the environment in which the robot is operating).

The sensor(s) 112 may provide sensor data to the processor(s) 102 (perhaps by way of data 107) to allow for interaction of the robotic system 100 with its environment, as well as monitoring of the operation of the robotic system 100. The sensor data may be used in evaluation of various factors for activation, movement, and deactivation of mechanical components 110 and electrical components 116 by control system 118. For example, the sensor(s) 112 may capture data corresponding to the terrain of the environment or location of nearby objects, which may assist with environment recognition and navigation. In an example configuration, sensor(s) 112 may include RADAR (e.g., for long-range object detection, distance determination, and/or speed determination), LIDAR (e.g., for short-range object detection, distance determination, and/or speed determination), SONAR (e.g., for underwater object detection, distance determination, and/or speed determination), VICON® (e.g., for motion capture), one or more cameras (e.g., stereoscopic cameras for 3D vision), a global positioning system (GPS) transceiver, and/or other sensors for capturing information of the environment in which the robotic system 100 is operating. The sensor(s) 112 may monitor the environment in real time, and detect obstacles, elements of the terrain, weather conditions, temperature, and/or other aspects of the environment.

Further, the robotic system 100 may include sensor(s) 112 configured to receive information indicative of the state of the robotic system 100, including sensor(s) 112 that may monitor the state of the various components of the robotic system 100. The sensor(s) 112 may measure activity of systems of the robotic system 100 and receive information based on the operation of the various features of the robotic system 100, such the operation of extendable legs, arms, or other mechanical and/or electrical features of the robotic system 100. The data provided by the sensor(s) 112 may enable the control system 118 to determine errors in operation as well as monitor overall operation of components of the robotic system 100.

As an example, the robotic system 100 may use force sensors to measure load on various components of the robotic system 100. In some implementations, the robotic system 100 may include one or more force sensors on an arm or a leg to measure the load on the actuators that move one or more members of the arm or leg. As another example, the robotic system 100 may use one or more position sensors to sense the position of the actuators of the robotic system. For instance, such position sensors may sense states of extension, retraction, or rotation of the actuators on arms or legs.

As another example, the sensor(s) 112 may include one or more velocity and/or acceleration sensors. For instance, the sensor(s) 112 may include an inertial measurement unit (IMU). The IMU may sense velocity and acceleration in the world frame, with respect to the gravity vector. The velocity and acceleration sensed by the IMU may then be translated to that of the robotic system 100 based on the location of the IMU in the robotic system 100 and the kinematics of the robotic system 100.

The robotic system 100 may include other types of sensors not explicated discussed herein. Additionally or alternatively, the robotic system may use particular sensors for purposes not enumerated herein.

The robotic system 100 may also include one or more power source(s) 114 configured to supply power to various components of the robotic system 100. Among other possible power systems, the robotic system 100 may include a hydraulic system, electrical system, batteries, and/or other types of power systems. As an example illustration, the robotic system 100 may include one or more batteries configured to provide charge to components of the robotic system 100. Some of the mechanical components 110 and/or electrical components 116 may each connect to a different power source, may be powered by the same power source, or be powered by multiple power sources.

Any type of power source may be used to power the robotic system 100, such as electrical power or a gasoline engine. Additionally or alternatively, the robotic system 100 may include a hydraulic system configured to provide power to the mechanical components 110 using fluid power. The power source(s) 114 may charge using various types of charging, such as wired connections to an outside power source, wireless charging, combustion, or other examples.

The electrical components 116 may include various mechanisms capable of processing, transferring, and/or providing electrical charge or electric signals. Among possible examples, the electrical components 116 may include electrical wires, circuitry, and/or wireless communication transmitters and receivers to enable operations of the robotic system 100. The electrical components 116 may interwork with the mechanical components 110 to enable the robotic system 100 to perform various operations. The electrical components 116 may be configured to provide power from the power source(s) 114 to the various mechanical components 110, for example. Further, the robotic system 100 may include electric motors. Other examples of electrical components 116 may exist as well.

Although not shown in FIG. 1, the robotic system 100 may include a body, which may connect to or house appendages and components of the robotic system. As such, the structure of the body may vary within examples and may further depend on particular operations that a given robot may have been designed to perform. For example, a robot developed to carry heavy loads may have a wide body that enables placement of the load. Similarly, a robot designed to reach high speeds may have a narrow, small body that does not have substantial weight. Further, the body and/or the other components may be developed using various types of materials, such as metals or plastics. Within other examples, a robot may have a body with a different structure or made of various types of materials.

The body and/or the other components may include or carry the sensor(s) 112. These sensors may be positioned in various locations on the robotic system 100, such as on the body and/or on one or more of the appendages, among other examples.

On its body, the robotic system 100 may carry a load, such as a type of cargo that is to be transported. The load may also represent external batteries or other types of power sources (e.g., solar panels) that the robotic system 100 may utilize. Carrying the load represents one example use for which the robotic system 100 may be configured, but the robotic system 100 may be configured to perform other operations as well.

As noted above, the robotic system 100 may include various types of legs, arms, wheels, and so on. In general, the robotic system 100 may be configured with zero or more legs. An implementation of the robotic system with zero legs may include wheels, treads, or some other form of locomotion. An implementation of the robotic system with two legs may be referred to as a biped, and an implementation with four legs may be referred as a quadruped. Implementations with six or eight legs are also possible. For purposes of illustration, biped and quadruped implementations of the robotic system 100 are described below.

Figure 2:
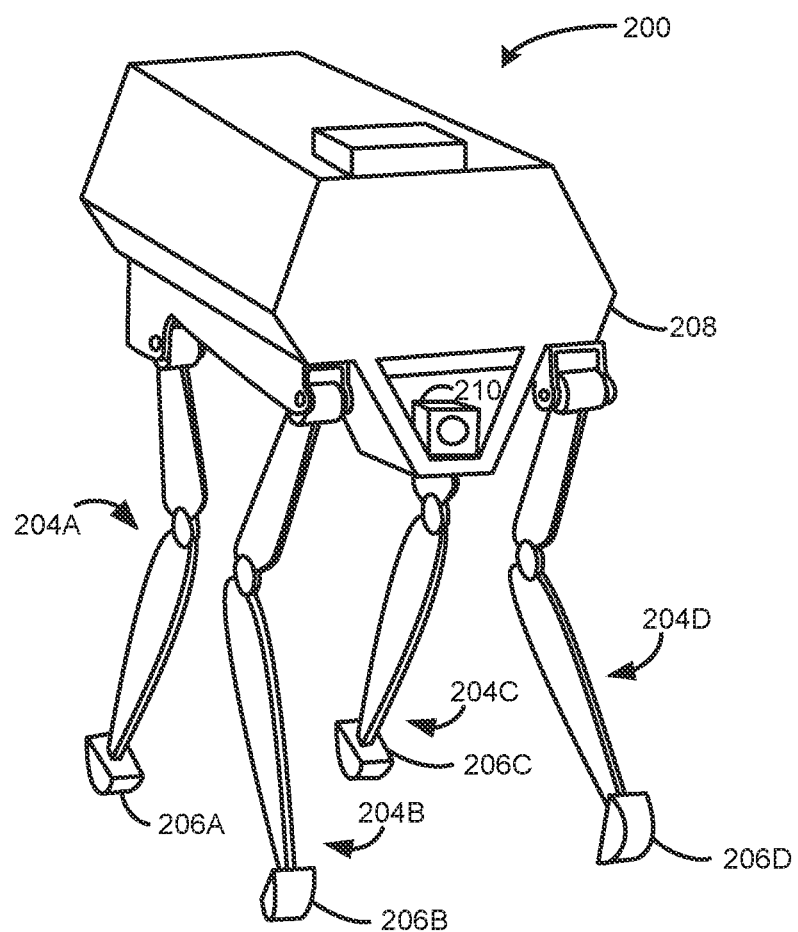
FIG. 2 illustrates a quadruped robot, in accordance with an example implementation.

FIG. 2 illustrates a quadruped robot 200, according to an example implementation. Among other possible features, the robot 200 may be configured to perform some of the operations described herein. The robot 200 includes a control system, and legs 204A, 204B, 204C, 204D connected to a body 208. Each leg may include a respective foot 206A, 206B, 206C, 206D that may contact a surface (e.g., a ground surface). Further, the robot 200 is illustrated with sensor(s) 210, and may be capable of carrying a load on the body 208. Within other examples, the robot 200 may include more or fewer components, and thus may include components not shown in FIG. 2.

The robot 200 may be a physical representation of the robotic system 100 shown in FIG. 1, or may be based on other configurations. Thus, the robot 200 may include one or more of mechanical components 110, sensor(s) 112, power source(s) 114, electrical components 116, and/or control system 118, among other possible components or systems.

The configuration, position, and/or structure of the legs 204A-204D may vary in example implementations. The legs 204A-204D enable the robot 200 to move relative to its environment, and may be configured to operate in multiple degrees of freedom to enable different techniques of travel. In particular, the legs 204A-204D may enable the robot 200 to travel at various speeds according to the mechanics set forth within different gaits. The robot 200 may use one or more gaits to travel within an environment, which may involve selecting a gait based on speed, terrain, the need to maneuver, and/or energy efficiency.

Further, different types of robots may use different gaits due to variations in design. Although some gaits may have specific names (e.g., walk, trot, run, bound, gallop, etc.), the distinctions between gaits may overlap. The gaits may be classified based on footfall patterns—the locations on a surface for the placement the feet 206A-206D. Similarly, gaits may also be classified based on ambulatory mechanics.

The body 208 of the robot 200 connects to the legs 204A-204D and may house various components of the robot 200. For example, the body 208 may include or carry sensor(s) 210. These sensors may be any of the sensors discussed in the context of sensor(s) 112, such as a camera, LIDAR, or an infrared sensor. Further, the locations of sensor(s) 210 are not limited to those illustrated in FIG. 2. Thus, sensor(s) 210 may be positioned in various locations on the robot 200, such as on the body 208 and/or on one or more of the legs 204A-204D, among other examples.

Figure 3:
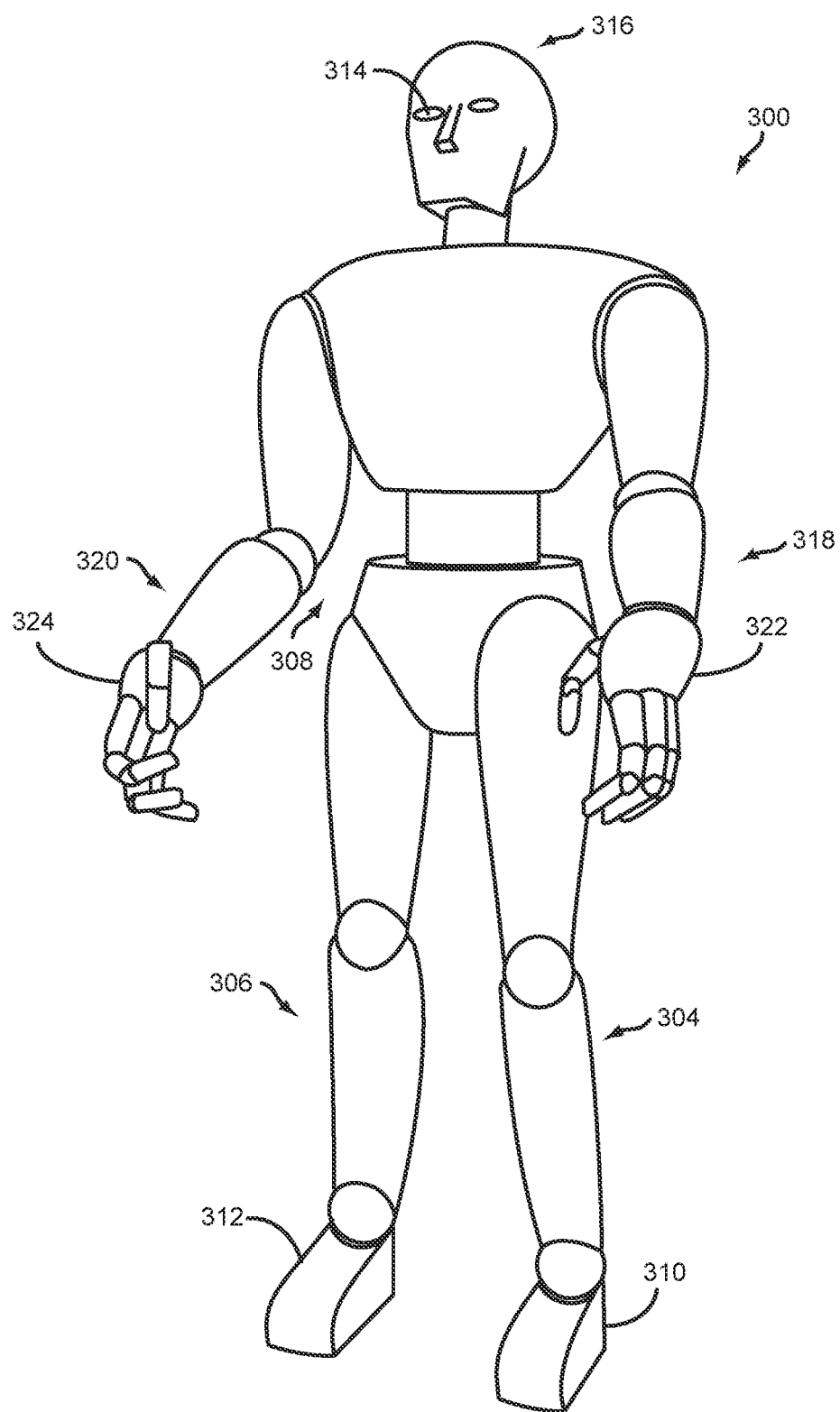
FIG. 3 illustrates a biped robot, in accordance with another example implementation.

FIG. 3 illustrates a biped robot 300 according to another example implementation. Similar to robot 200, the robot 300 may correspond to the robotic system 100 shown in FIG. 1, and may be configured to perform some of the implementations described herein. Thus, like the robot 200, the robot 300 may include one or more of mechanical components 110, sensor(s) 112, power source(s) 114, electrical components 116, and/or control system 118.

For example, the robot 300 may include legs 304 and 306 connected to a body 308. Each leg may consist of one or more members connected by joints and configured to operate with various degrees of freedom with respect to one another. Each leg may also include a respective foot 310 and 312, which may contact a surface (e.g., the ground surface). Like the robot 200, the legs 304 and 306 may enable the robot 300 to travel at various speeds according to the mechanics set forth within gaits. The robot 300, however, may utilize different gaits from that of the robot 200, due at least in part to the differences between biped and quadruped capabilities.

The robot 300 may also include arms 318 and 320. These arms may facilitate object manipulation, load carrying, and/or balancing for the robot 300. Like legs 304 and 306, each arm may consist of one or more members connected by joints and configured to operate with various degrees of freedom with respect to one another. Each arm may also include a respective hand 322 and 324. The robot 300 may use hands 322 and 324 (or end-effectors) for gripping, turning, pulling, and/or pushing objects. The hands 322 and 324 may include various types of appendages or attachments, such as fingers, grippers, welding tools, cutting tools, and so on.

The robot 300 may also include sensor(s) 314, corresponding to sensor(s) 112, and configured to provide sensor data to its control system. In some cases, the locations of these sensors may be chosen in order to suggest an anthropomorphic structure of the robot 300. Thus, as illustrated in FIG. 3, the robot 300 may contain vision sensors (e.g., cameras, infrared sensors, object sensors, range sensors, etc.) within its head 316.

II. EXAMPLE ELECTROMECHANICAL ACTUATORS FOR A ROBOT

In examples, hydraulic actuators could be used to actuate members of a robot. A hydraulic system may include a pump and accumulator at a central location on the robot and configured to provide pressurized hydraulic fluid through pipes and/or hoses to hydraulic actuators coupled to the members of the robot. In this configuration, the actuation inertia of the pump and accumulator is decoupled from inertia provided to the ground surface as the robot moves. Due to the decoupling of inertias, hydraulic robotic systems are characterized by high bandwidth for position and force control responsiveness. However, hydraulic systems have disadvantages such as potential hydraulic fluid leaks, complexity of plumbing, and unsuitability of existing hydraulic power units to smaller robots.

Electromechanical actuators alleviate at least some disadvantages of hydraulic actuators because there are no leaks or complex plumbing involved with operating electromechanical actuators. Further, electromechanical systems may be more efficient than hydraulic systems. However, electromechanical actuators may have disadvantages compared to hydraulic systems. For instance, while the rotating inertia of a robot member driven by a hydraulic actuator might have a linear relationship with a diameter of the actuator for a given strength, the rotating inertia of a robot member driven by an electromechanical actuator may be proportional to the square of the diameter of the actuator's rotating assembly and is influenced by the gear ratio of the transmission for the given strength. Further, reflected inertia of a hydraulic actuator might be negligible compared to the inertial of a member (e.g., leg) of a robot, whereas reflected inertial of an electromechanical may depend on inertias of the motor and the transmission multiplied by the square of the gear ratio of the transmission. Thus, for large robots, electromechanical actuators may have a high inertia that limits responsiveness and performance characteristics of the robot.

For robots smaller in size, electromechanical actuators could be designed, as described in this disclosure, to achieve high performance characteristics compared to corresponding hydraulic actuators. Disclosed herein are systems, actuators, configurations, and apparatuses that reduce rotating inertia of robot members to allow for achieving high peak torques capable of providing sufficiently high accelerations suitable for high performance robots.

a. Example Screw Actuator for a Joint of a Robot

In examples, a knee joint of a robot may experience high accelerations that results, for example, from actuating the robot to move fast (e.g., run or jog). High accelerations could also result when the robot is subjected to a disturbance at its leg, and the robot responds with moving the leg, and particularly the knee joint, at a high acceleration to maintain balance. In some examples, an electric motor could be coupled to the knee joint of robot, such that rotational motion of the motor causes a lower leg member of the robot to rotate relative to an upper leg member that is coupled to the lower leg member at the knee joint. In this configuration, the rotational inertia of the motor may limit the responsiveness of the robot, and may thus reduce effectiveness of force control strategies of the lower leg member.

Further, if a transmission is coupled to the motor, and that transmission has a particular gear ratio that allows for speed reduction and torque amplification, the rotational inertia at the knee joint is proportional to the square of the gear ratio. So, a higher gear ratio that allows for higher torques may lead to a higher rotational inertia, thus reducing the responsiveness of the robot.

Reducing the rotational inertia at the knee joint may improve responsiveness of the robot. In an example, a screw actuator could be used to drive the knee joint of the robot, because screw actuators are light and slender and thus have low inertia compared to other actuator configurations. Further, using a screw actuator allows for a reduced distal mass at the knee, which may in turn allow for higher acceleration capabilities.

Figure 4A:
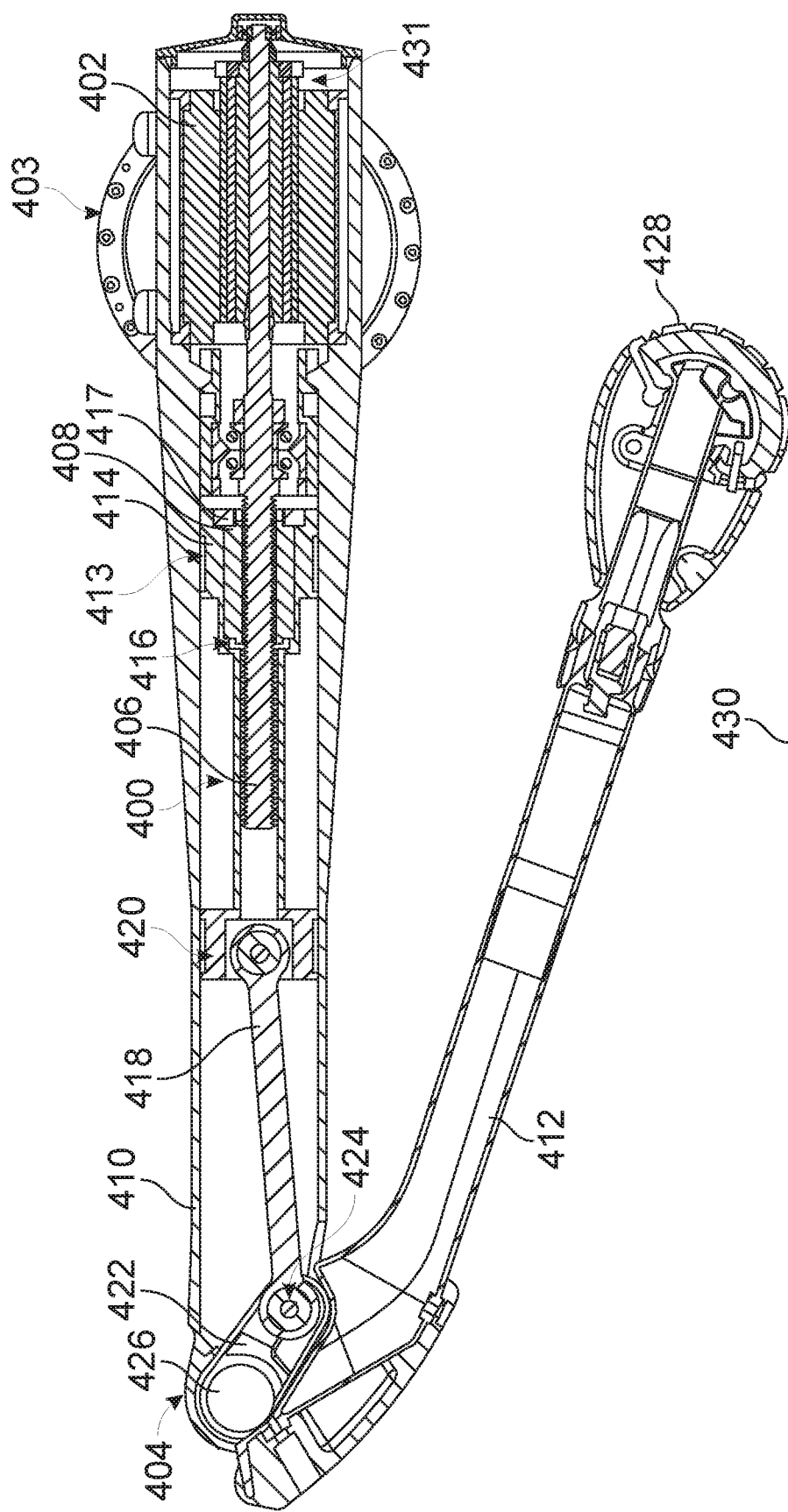
FIG. 4A illustrates a cross section of a robot leg having a screw actuator, in accordance with an example implementation.

FIG. 4A illustrates a cross section of a robot leg having a screw actuator 400, in accordance with an example implementation. An electric motor 402 is located at or near a hip joint 403 of the robot. In other examples, the electric motor 402 may be located at an upper leg portion of the robot. Whether the electric motor 402 is located at an upper leg portion or the hip joint 403, the mass of the motor 402 is shifted away from a knee joint 404. Thus, these configurations may reduce the distal mass at the knee joint 404 of the robot, and therefore the rotational inertia at the hip joint 403 is reduced.

The screw actuator 400 is a mechanical linear actuator that translates rotational motion to linear motion with little friction. In an example, the screw actuator 400 may be a planetary roller screw type and may include a screw shaft 406 and a nut 408. The screw shaft 406 may have a multi-start V-shaped thread on a periphery thereof. The V-shaped thread provides a helical raceway for multiple rollers radially arrayed around the screw shaft 406 and encapsulated by the nut 408. The rollers are not shown in FIG. 4A to reduce visual clutter in the drawings.

The nut 408 is threaded on an interior peripheral surface thereof to interface with the V-shaped thread of the screw shaft 406. The pitch of the thread of the screw shaft 406 may be the same as the pitch of the internal thread of the nut 408. The rollers spin in contact with, and serve as low-friction transmission elements between, the screw shaft 406 and the nut 408. The rollers may have a single-start thread with convex flanks that limit friction at the rollers' contacts with the screw shaft 406 and the nut 408. The rollers may orbit the screw shaft 406 as they spin (in the manner of planet gears to a sun gear), and could thus be referred to as planetary, or satellite, rollers.

The motor 402 is coupled to the screw shaft 406, and thus as the motor 402 rotates, the screw shaft 406 rotates therewith. Rotation of the screw shaft 406 results in axial or longitudinal travel of the nut 408.

The motor 402 and the screw actuator 400 are housed within a body (e.g., a machined aluminum body) of an upper leg member 410 of the robot. The upper leg member 410 is coupled to a lower leg member 412 at the knee joint 404.

The nut 408 is housed within a proximal end 413 of a carrier 414 and interfaces with the carrier 414 at a shoulder 416 such that as the nut 408 travels along the screw shaft 406, the carrier 414 also moves linearly within the upper leg member 410. Herein, the term "proximal end" refers to the end of the carrier 414 closer to the motor 402.

The nut 408 is axially constrained within the proximal end 413 of the carrier 414 by the shoulder 416 and a nut 417 that captures the nut 408 axially in the carrier 414. Further, the nut 408 may be rotationally constrained to the carrier 414 to preclude rotation of the nut 408 relative to the carrier 414. For instance, the nut 408 may be coupled to the carrier 414 via a key-keyway configuration.

A linkage mechanism is coupled to the carrier 414 to facilitate converting the linear motion of the carrier 414 into a rotation motion of the lower leg member 412 relative to the upper leg member 410 about the knee joint 404. As an example, the linkage mechanism may include a first link 418 (e.g., a connecting rod) that is coupled to a distal end 420 of the carrier 414. Herein, the term "distal end" refers to the end of the carrier 414 that is farthest from the motor 402. In another example, the first link 418 may be trunnion-mounted to the carrier 414 at other locations that are closer to the motor 402.

The first link 418 may be coupled to a second link 422 at a joint 424, and the second link may be coupled at the knee joint 404 at knee pivot 426. The lower leg member 412 is also coupled to the knee joint 404 at the knee pivot 426. In this configuration, the linear motion of the carrier 414 causes the first link 418 to move, thereby causing the second link 422 and the lower leg member 412 to rotate about the knee pivot 426. Other linkage configurations could be used. For instance, a four bar mechanism could be used to achieve different transmission curve shapes.

The direction of rotation of the motor 402 determines the direction of rotation of the lower leg member 412 relative to the upper leg member 410. For instance, if the motor 402 rotates in a given direction (e.g., clockwise), the nut 408 and the carrier 414 may extend and push the first link 418. As a result, the second link 422 rotates in a clockwise direction from a perspective of a viewer of FIG. 4A about the knee pivot 426. As a result, the lower leg member 412 may also rotate clockwise from a perspective of a viewer of FIG. 4A, thus for example pushing a foot 428 against a surface 430.

Conversely, if the motor 402 rotates in the opposite direction (e.g., counter-clockwise), the nut 408 and the carrier 414 may retract and pull the first link 418. As a result, the second link 422 rotates in a counter-clockwise direction from a perspective of a viewer of FIG. 4A about the knee pivot 426, thereby causing the lower leg member 412 to curl upward. Thus, alternating between rotating the motor 402 clockwise and counter-clockwise causes the robot to take steps (e.g., walk or run at a particular pace).

In an example, the motor 402 may include an encoder 431. The encoder 431 is configured to generate a signal indicative of a rotary position of a rotor of the motor 402. The encoder 431 may provide information indicative of the rotary position of the rotor to a controller of the robot. The controller may implement a closed-loop feedback control on the rotary position of the motor 402 so as to accurately position the nut 408 within the upper leg member 410.

By placing the motor 402 closer to the hip joint 403 and using the screw actuator 400, the distal mass at the knee joint 404 is reduced. Further, using the screw actuator 400 as a speed reducer instead of a rotary gearbox may reduce the effective rotational inertia because the screw actuator 400 has a reduced rotational inertia compared to a rotary gearbox.

Figure 4B:
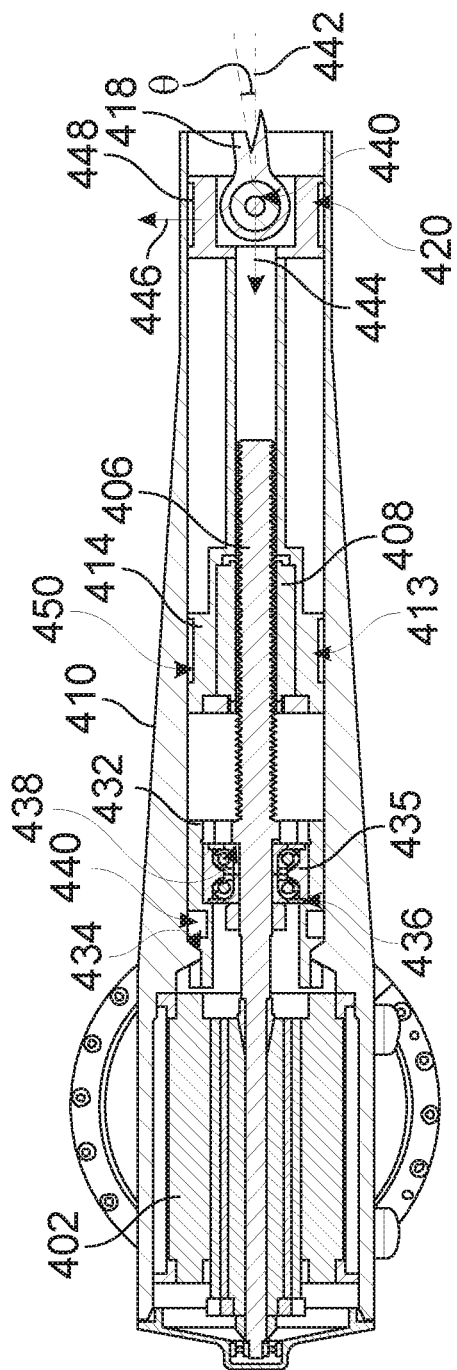
FIG. 4B illustrates a cross section of an upper leg member, in accordance with an example implementation.

FIG. 4B illustrates a cross section of the upper leg member 410, in accordance with an example implementation. As shown in FIG. 4B, the upper leg member 410 may house a bearing carrier 432. The bearing carrier 432 may be seated along a conical seat 434 that protrudes inward from an internal surface of the upper leg member 410.

The bearing carrier 432 houses a bearing 435 configured to allow the screw shaft 406 to rotate freely. An outer diameter of an outer race of the bearing 435 interfaces with an interior peripheral surface of the bearing carrier 432. The outer race of the bearing 435 is retained against a shoulder 436 formed of a stepped surface on the interior peripheral surface of the bearing carrier 432.

Further, the screw shaft 406 includes a shoulder 438 formed of a stepped surface on an exterior peripheral surface of the screw shaft 406. The shoulder 438 interfaces with an inner race of the bearing 435. This way, the bearing 435 is axially constrained between the shoulder 438 and the shoulder 436.

As shown in FIG. 4B, the first link 418 is coupled to the distal end 420 of the carrier 414 via a pin 440. The first link 418 forms an angle □ relative to a longitudinal axis 442 of the screw shaft 406. Thus, as the screw shaft 406 rotates causing the nut 408 and the carrier 414 to push the first link 418, the first link 418 may impart a reaction force onto carrier 414, which is transferred to the nut 408 and the screw shaft 406. The reaction force can be resolved into a longitudinal axial force component 444 acting along the longitudinal axis 442 and a radial or off-axis force component 446 acting perpendicular to the longitudinal axis 442 and the interior surface of the upper leg member 410.

To reduce effects of the off-axis force component 446 and the friction that results thereof, a slider bearing 448 is mounted between an external peripheral surface of the carrier 414 at the distal end 420 and the interior peripheral surface of the upper leg member 410. The slider bearing 448 may be configured to reduce friction and facilitate axial motion of the carrier 414 within the upper leg member 410. Particularly, the slider bearing 448 may be configured to react the off-axis force component 446 on the nut 408 to the upper leg member 410 and constrain the forces resulting from interaction between the first link 418 and the carrier 414 along the axis 442. In an example, the slider bearing 448 may be made of Teflon®.

In an example, another slider bearing 450 could be mounted between an external peripheral surface of the carrier 414 at the proximal end 413 and the interior peripheral surface of the upper leg member 410. In these examples, the slider bearings 448 and 450 may operate as guide bushings that allow the carrier 414 to be subjected to the axial force component 444 while reacting the off-axis force component 446 and reducing friction.

As mentioned above, the axial force component 444 acting on the carrier 414 is transferred to the nut 408 and the screw shaft 406. The screw shaft 406 interfaces with the bearing 435 at the shoulder 438, and thus the bearing 432 is subjected to the axial force component 444. The axial force component 444 is then transferred from the bearing 435 via the shoulder 436 to the bearing carrier 432.

An axial load cell 440 may be disposed on the exterior peripheral surface of the bearing carrier 432. Thus, the axial load cell 440 is also subjected to the axial force component 444, which is imparted to the carrier 414 and the screw shaft 406 during operation of the robot leg. The axial load cell 440 may generate an electric signal that is proportional to the axial force component 444 imparted to the screw shaft 406. The electric signal may be provided to a controller of the robot or the leg members of the robot.

In an example, the controller may use the encoder 431 and the axial load cell 440 to implement various control strategies based on condition of the robot, the environment of the robot, and the commanded acceleration. For example, in a first control strategy, the controller may implement a closed-loop position control on the rotary position of the motor 402 as mentioned above. In a second control strategy, the controller may implement closed-loop force control for the force exerted by the foot 428 on the surface 430. This control strategy may allow for high acceleration capabilities for the robot leg. In a third control strategy, the controller may implement closed-loop position and force control where the force control loop may be used to dampen motion of the robot leg. These control strategies are examples for illustration, and other control strategies could be implemented.

Figure 5A:
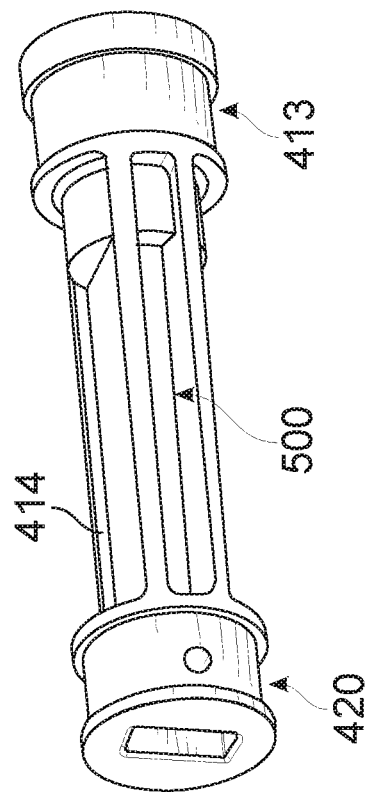
FIG. 5A illustrates a carrier having at least one longitudinal channel disposed on an outer surface of the carrier, in accordance with an example implementation.
Figure 5B:
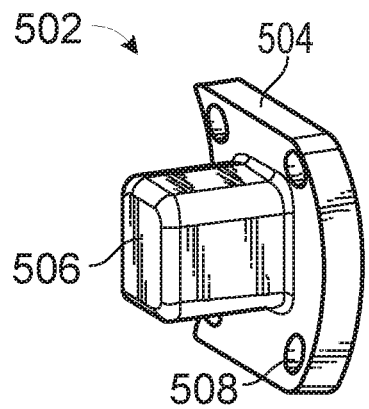
FIG. 5B illustrates an anti-rotation element, in accordance with an example implementation.
Figure 5C:
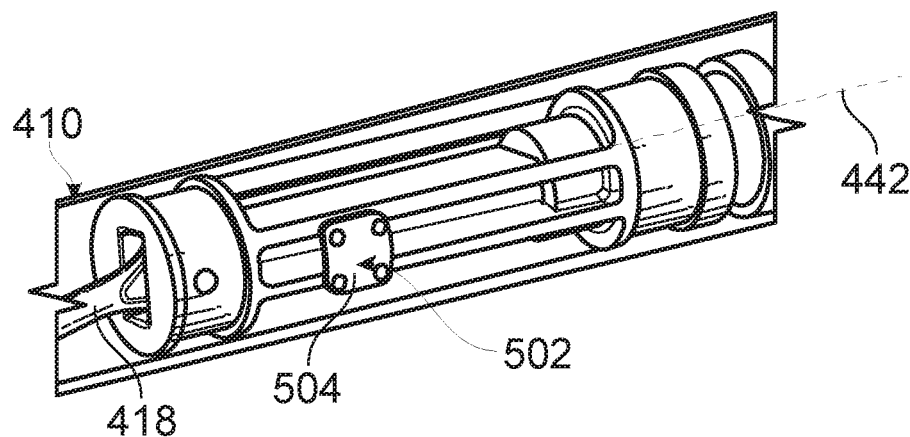
FIG. 5C illustrates a transparent view of an upper leg member and an anti-rotation element coupled thereto, in accordance with an example implementation.

In examples, the carrier 414, and the components coupled thereto such as the nut 408, may be precluded from rotation about the longitudinal axis 442 via anti-rotation mechanisms or configurations. FIGS. 5A-5C illustrate an anti-rotation configuration for the carrier 414, in accordance with an example implementation. Specifically, FIG. 5A illustrates the carrier 414 having at least one longitudinal channel 500 disposed on an outer surface of the carrier 414, in accordance with an example implementation. As shown in FIG. 5A, the longitudinal channel 500 is disposed between the proximal end 413 and the distal end 420 of the carrier 414. In examples, the longitudinal channel 500 may take the form of a slot that is machined longitudinally on the outer surface of the carrier 414.

FIG. 5B illustrates an anti-rotation element 502, in accordance with an example implementation. The anti-rotation element 502 includes a curved plate 504 and a nub 506 that protrudes from a concave surface of the curved plate 504. The anti-rotation element 502 is configured to be coupled to an outer surface of the upper leg member 410 such that the nub 506 protrudes radially inward within the upper leg member 410 and engages the longitudinal channel 500.

As an example, the curved plate 504 may have holes such as hole 508. The outer surface of the upper leg member 410 may have corresponding holes. Fasteners could be used to couple the curved plate 504 to the upper leg member 410 via the holes in the curved plate 504 and the corresponding holes in the upper leg member 410. Further, the upper leg member 410 may have a central hole that corresponds to and is configured to receive the nub 506 therethrough.

FIG. 5C illustrates a transparent view of the upper leg member 410 and the anti-rotation element 502 coupled thereto, in accordance with an example implementation. The outer surface of the upper leg member 410, or a portion thereof, may be curved to match the curvature of the concave surface of the curved plate 504. This way, the concave surface of the curved plate 504 may conform to a profile or contour of the outer surface of the upper leg member 410 when coupled thereto.

The nub 506 protrudes through the outer surface of the upper leg member 410 and engages with the longitudinal channel 500 of the carrier 414. With this configuration, as the carrier 414 moves axially within the upper leg member 410, the nub 506 precludes the carrier 414 from rotating about the longitudinal axis 442. In examples, the nub 506 may be made of a material (e.g., Teflon) that reduces friction with the longitudinal channel 500 as the carrier 410 moves within the upper leg member 410.

Figure 6C:
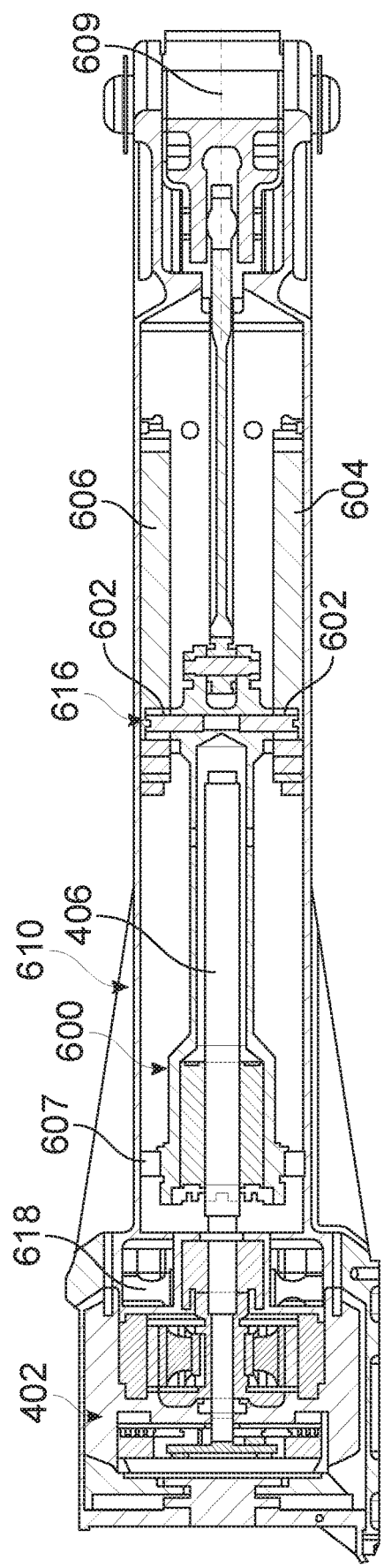
FIG. 6C illustrates a top view cross section of an upper leg member and components disposed therein, in accordance with an example implementation.

Other example anti-rotation mechanisms could be implemented. FIGS. 6A-6C illustrate another anti-rotation mechanism, in accordance with an example implementation. Specifically, FIG. 6A illustrates a carrier 600 having roller(s) 602 coupled thereto, in accordance with an example implementation. FIG. 6A shows one roller 602 on one side of the carrier 600. Another roller may be coupled to the carrier 600 on the other side thereof. In examples, more rollers similar to the roller 602 may be coupled to the carrier 600. The roller 602 is configured to roll within a rail 604, and the roller corresponding to the roller 602 on the other side of the carrier 600 is configured to roll within a rail 606 that is parallel to the rail 604. Both rollers are collectively referred to as roller(s) 602.

The rails 604 and 606 are configured to constrain the roller(s) 602 therein. In this manner, the rails 604 and 606 may operate as tracks for the roller(s) 602 such that the rails 604 and 606 and the roller(s) 602 form a roller element bearing configuration. This configuration reduces friction as the carrier 600 moves within the robot leg. Additionally, in an example, a slider bearing 607 made, for example, of Teflon®, could be disposed about an outer surface of the carrier 600 to interface with an interior surface of the robot leg to further reduce friction.

Both rails 604 and 606 have holes such as holes 608A, 608B, 608C, 608D, and 608E formed therein that may be configured to receive fasteners to fixedly mount the rails 604 and 606 to the robot leg as described below with respect to FIG. 6B. Because the rails 604 and 606 are fixedly mounted to the robot leg and at the same time they constrain motion of the roller(s) 602 therein, the carrier 600 is precluded from rotation about a longitudinal axis 609 thereof.

FIG. 6B illustrates an upper leg member 610 configured to receive the carrier 600 and the rails 604 and 606 therein, in accordance with an example implementation. The upper leg member 610 may be similar to the upper leg member 410, but may additionally have a pattern of holes 612 on an outside surface thereof. The pattern of holes 612 corresponds to the holes disposed in the rails 604 and 606. For instance, holes 614A, 614B, 614C, and 614D of the pattern of holes 612 may correspond to the holes 608A, 608B, 608C, and 608D of the rail 604, respectively. Fasteners could be then used to fixedly mount the rails 604 and 606 within the upper leg member 610.

FIG. 6C illustrates a top view cross section of the upper leg member 610 and components disposed therein, in accordance with an example implementation. As shown in FIG. 6C, a roller carriage 616 is coupled to a distal end of the carrier 600 and is disposed perpendicular to the longitudinal axis 609. The roller(s) 602 are coupled to the roller carriage 616 and configured to roll within the rails 604 and 606, while being constrained therein. Particularly, at least one roller 602 is coupled to first end of the roller carriage 616 and rollers within the rail 604 and another roller 602 is coupled to a second end of the roller carriage 616 opposite the first end and configured to roll within the rail 606. While FIGS. 6A and 6C illustrate the rails 604 and 606 as separate components from the upper leg member 610, in some examples, the rails 604 and 606 could alternatively be integrated with or built-in the inner surface of the upper leg member 610.

An axial load cell 618 is disposed closer to the motor 402 compared to the axial load cell 440 described above. The axial load cell 618 may also be of a different type. For instance, while the axial load cell 440 is depicted as a column-style load cell, the axial load cell 618 is a bending beam style load cell. Other styles and locations for load cells could be used as well.

As the robot moves and the lower leg member 412 shown in FIG. 4A rotates relative to the upper leg member 410 or 610, the screw shaft 406 is subjected to alternating compressive and tensile forces. For instance, if the screw shaft 406 is rotating in a direction (e.g., counter-clockwise) that causes the nut 406 to retract, thus pulling the carrier 414 and the first link 418, the screw shaft 406 is under tension. Whereas, if the screw shaft 406 is rotating in an opposite direction (e.g., clockwise) that causes the nut 406 to extend, thus pushing the carrier 414 and the first link 418, the screw shaft 406 is under compression.

Further, for the robot to move, the lower leg member 412, which may be in contact with a ground surface (e.g., the surface 430), pushes against the ground surface. Even when the robot is standing in place, the lower leg member 412 exerts a pushing force against the ground surface to maintain the robot standing and balanced. Whether the robot is moving or standing, the pushing force against the ground surface may cause either a tensile or compressive force in the screw shaft 406 based on a geometric configuration of the first link 418 relative to the knee pivot 426.

Figure 7:
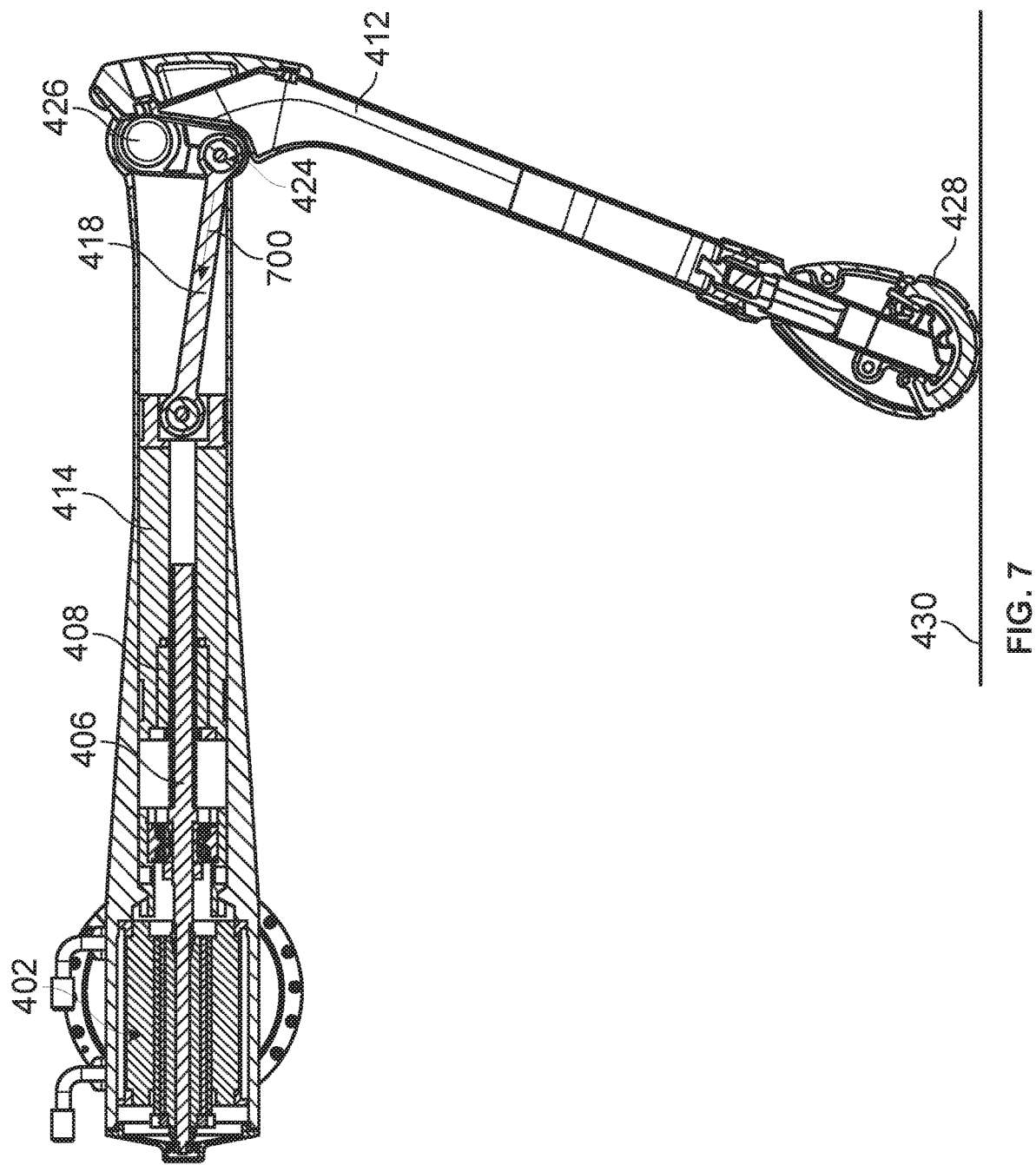
FIG. 7 illustrates a configuration with a screw shaft under compression, in accordance with an example implementation.

FIG. 7 illustrates a configuration with the screw shaft 406 under compression, in accordance with an example implementation. The configuration shown in FIG. 7 is similar to the configuration of FIG. 4A. In this configuration, the first link 418 is coupled to the lower leg member 412 at the joint 424, which is located between the knee pivot 426 and the foot 428. As a result, when the lower leg member 412 pushes against the surface 430, a compressive force is applied along a length of the first link 418 in a direction of arrow 700. This compressive force is transmitted to the carrier 414 and through the nut 408 to the screw shaft 406. Thus, in this configuration, the screw shaft 406 is under compression.

Figure 8:
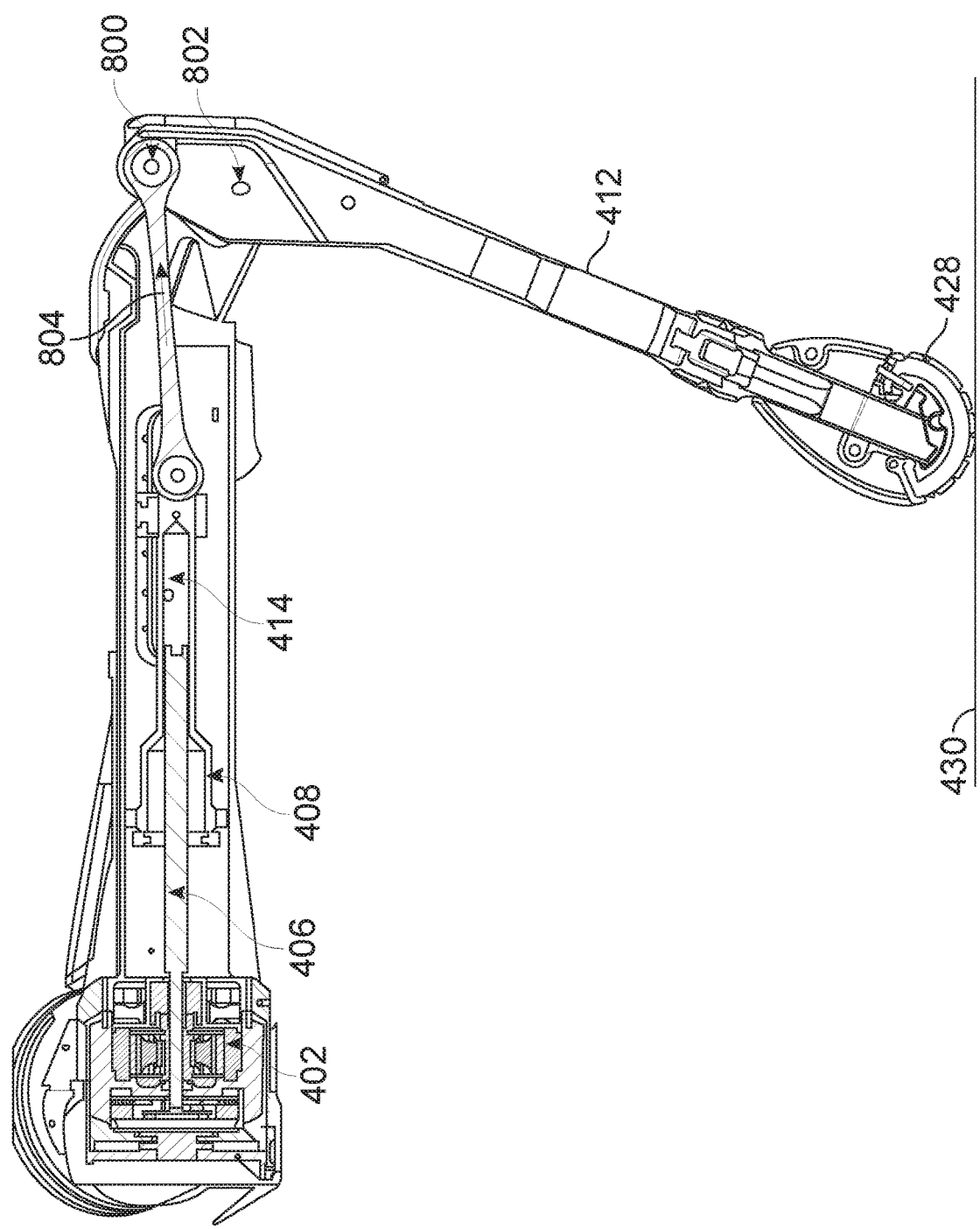
FIG. 8 illustrates a configuration with a screw shaft under tension, in accordance with an example implementation.

FIG. 8 illustrates a configuration with the screw shaft 406 under tension, in accordance with an example implementation. In this configuration, the first link 418 is coupled to the lower leg member 412 at a joint 800 such that a knee pivot 802 is disposed between the joint 800 and the foot 428. As a result, when the lower leg member 412 pushes against the surface 430, a tensile force is applied along a length of the first link 418 in a direction of arrow 804. This tensile force is transmitted to the carrier 414 through the nut 408 to the screw shaft 406. Thus, in this configuration, the screw shaft 406 is under tension.

Either of the configurations of FIG. 7 or 8 could be used. However, in some examples, the robot may be subjected to environmental conditions that could cause forces in the screw shaft 406 that might be sufficiently high to cause buckling therein. In these examples, the configuration of FIG. 8 could be used so as to preclude buckling in the screw shaft 406. The peak extension force of leg of the robot is typically higher than the peak retraction force and the configuration of FIG. 8 puts the screw shaft 406 in tension during high extension force events.

Figure 9:
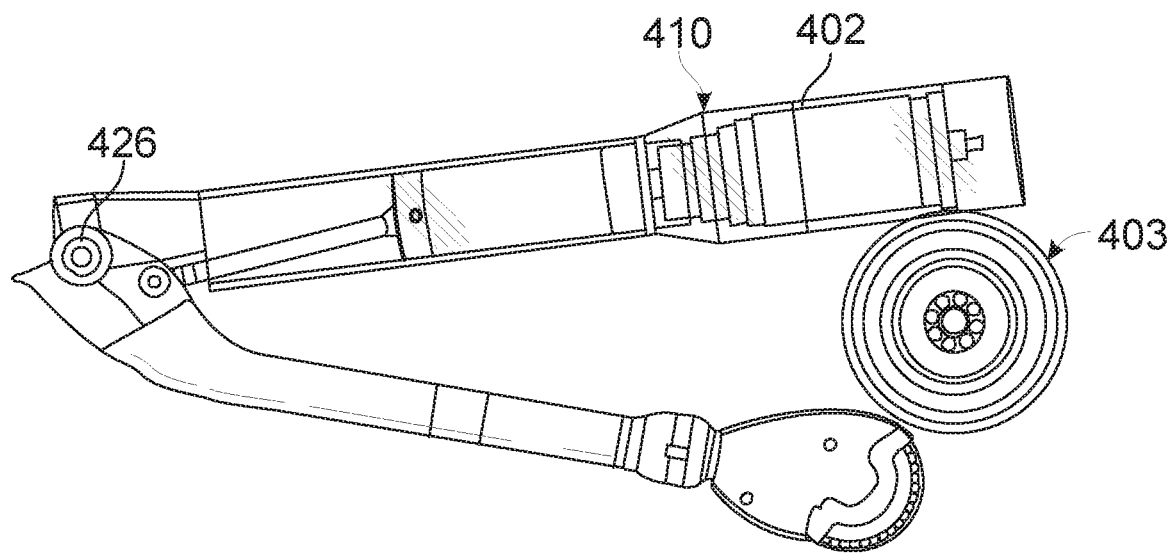
FIG. 9 illustrates an upper leg member offset relative to a hip joint, in accordance with an example implementation.

Other configurations for the robot leg could be implemented. FIG. 9 illustrates the upper leg member 410 offset relative to the hip joint 403, in accordance with an example implementation. As shown, the assembly including the upper leg member 410, and the components therein, is offset relative to the hip joint 403. This configuration may alleviate packaging constraints imposed by limiting a length of the upper leg member 410 based on the location of the hip joint 403. In other words, the length of the upper leg member 410 could be increased in the configuration of FIG. 9 relative to the configuration of FIG. 4A, for example. Alternatively, in other examples, offsetting the upper leg member 410 relative to the hip joint 403 may facilitate reducing an overall length from the knee pivot 426 to the hip joint 403.

Further, in the configurations discussed above, the motor 402 is disposed inline with the screw shaft 406. In some examples, these configurations could cause the upper leg member 410 or 610 to be relatively long. Other configurations could be used to shorten the upper leg member 410 or 610.

Figure 10:
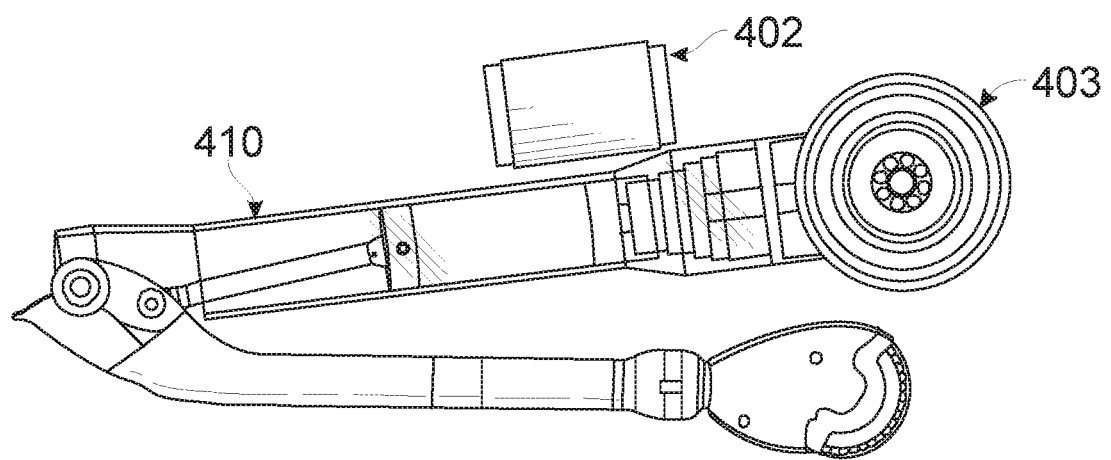
FIG. 10 illustrates a motor offset from an upper leg member, in accordance with an example implementation.

FIG. 10 illustrates the motor 402 offset from the upper leg member 410, in accordance with an example implementation. As shown, by removing the motor 402 from the upper leg member 410 and offsetting it relative to the upper leg member 410, the upper leg member 410 could be shortened. In this configuration a belt drive could be disposed as a speed reduction pre-stage between the motor 402 and the screw shaft 406. This speed reduction pre-stage could allow for reducing a speed reduction ratio of the screw actuator 400. Reducing the speed reduction ratio of the screw actuator 400 may reduce the rotational inertia, leading to higher performance characteristics as described below.

Generally, a roller screw may provide more bearing points or area than a ball screw within a given volume, and may thus lower contact stresses. Also, a roller screw can be more compact for a given load capacity while providing similar efficiency (e.g., 75%-90%) as ball screws at low to moderate speeds, and maintain relatively high efficiency at high speeds. A roller screw may further achieve better positioning accuracy, load rating, rigidity, speed, acceleration, and lifetime compared to a ball screw. However, a ball screw could be cheaper than a roller screw, and thus it may be desirable to use a ball screw for some applications.

b. Example Transmission with Integrated Clutch for Overload Protection

Rotational inertia affects the position and force control responsiveness of a robot. The effective rotational inertia at a joint of the robot may depend on the rotational inertia of the motor coupled to the joint and the rotational inertia of a transmission coupled to the motor. The transmission may have a particular gear ratio that allows for speed reduction and torque amplification, and the effective rotational inertia at the joint is proportional to the square of the gear ratio. So, a higher gear ratio that allows for higher torques may lead to a higher rotational inertia, thus reducing the responsiveness of the robot.

Typically, a large motor and low gear ratio may provide lower output inertia compared to a small motor and high gear ratio, but at the expense of greater mass. Thus, using a large motor to achieve higher torques and strengths may lead to a high rotational inertia, which reduces the responsiveness of the robot. Even if a small motor is used, a transmission with a high gear reduction ratio may also lead to a high effective rotational inertia.

In selecting a motor for a joint of a robot, one approach may entail determining a maximum torque that the joint is expected to be subjected to and select a motor that can achieve that maximum torque. However, this approach may lead to high effective rotational inertias. For example, in impact situations, such as when a leg of a robot hits a ground surface unexpectedly or the leg is subjected to a sudden impact by an object, the impact may cause the motor to spin at high speeds to respond to the impact and maintain the robot's balance. Particularly, the impact causes the motor and input side of the transmission to accelerate rapidly. The resulting inertial torque gets amplified by the gear ratio causing high torque at the joint, which may damage the transmission and/or the leg structure. The reflected inertia in this situation may be determined based on the sum of the rotational inertia of the motor and the transmission multiplied by the square of the reduction ratio of the transmission. Selecting a motor that can achieve a maximum torque that occurs in such impact situations may lead to a large motor with a corresponding large rotational inertia.

Another approach may entail impedance matching. Specifically, the motor and the transmission at a joint are selected to have a reflected or output inertia that is equal to the inertia of the robot member that is controlled by the joint. This approach may increase the acceleration capability of the joint.

In another example, the motor may be used to directly drive the member without a transmission coupled thereto. This way, the reflected inertia may be reduced. However, without a transmission, there is no torque amplification and the maximum torque is limited by the torque that the motor could achieve. Even if a transmission with a reduced gear ratio is used, the motor may then have a larger size to compensate for the reduced torque amplification at the transmission, thus leading to excessive weight and size.

An improved approach presented herein may entail integrating an overload protection system within the motor or the transmission. The overload protection system may isolate the transmission from high torques encountered in impact situations. This way, a reduced size transmission that can achieve appropriate torques and accelerations may be selected. A smaller transmission may have lower inertia, thus allowing for a smaller motor to achieve desired acceleration, because the overall inertial is reduced.

Disclosed herein are systems and apparatuses that involve integrating a clutch to a harmonic drive transmission to allow for reducing a size of the motor and transmission, thus reducing mass and inertia to improve responsiveness of the robot. The integrated clutch system described below, may, for example, be used at a hip joint of the robot or other joints.

Figure 11:
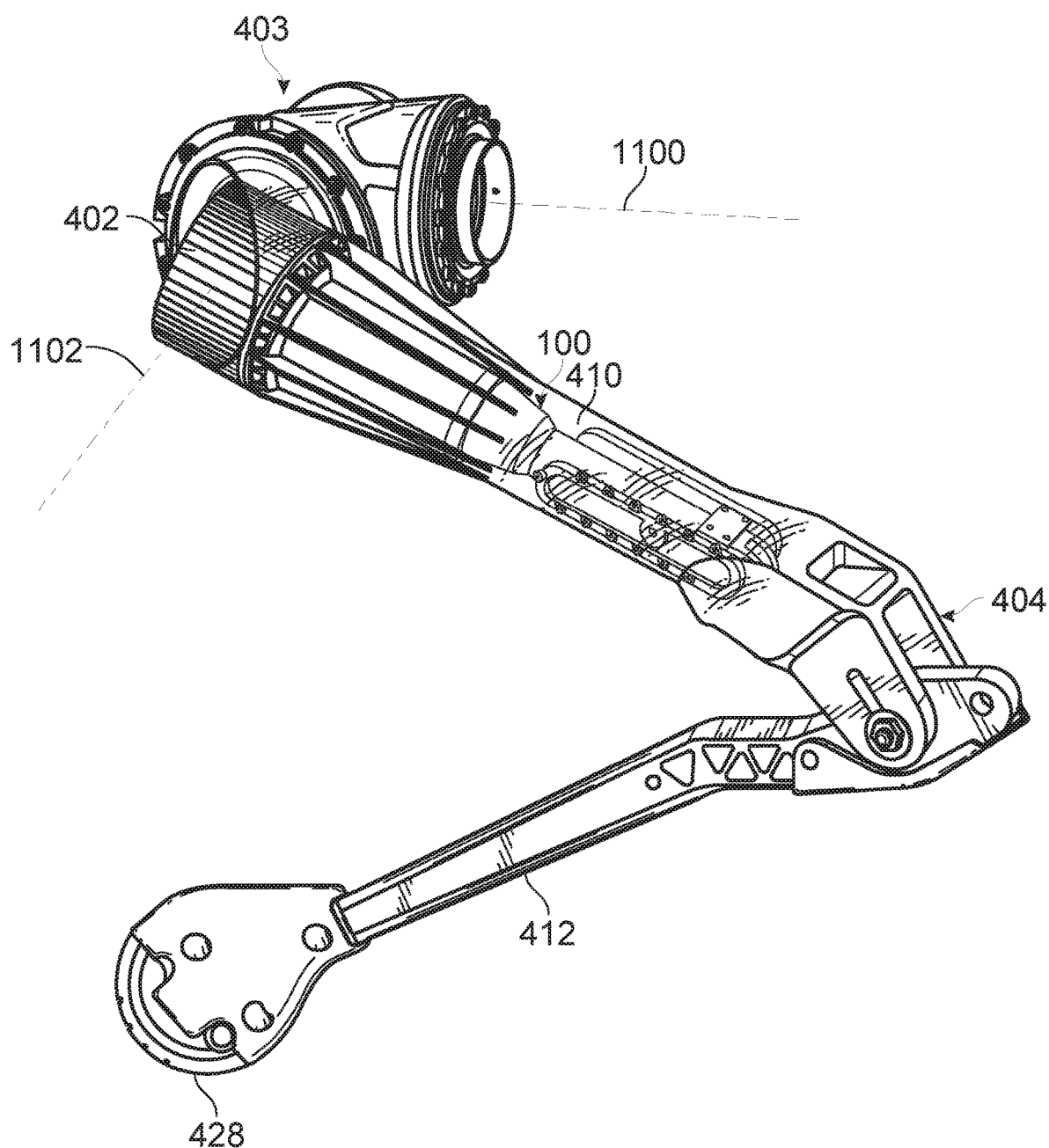
FIG. 11 illustrates a robot leg, in accordance with an example implementation.

FIG. 11 illustrates a robot leg, in accordance with an example implementation. As mentioned above, a screw actuator such as the screw actuator 400 may be used instead of a rotary gearbox to drive the knee joint 404. The screw actuator 400 may allow for reducing the distal mass at the knee joint 404. The distal mass affects the inertial of the leg, and placing mass closer to the hip reduces the inertial torque required at the hip joints. The screw actuator 400 may also reduce the effective rotational inertia because the screw actuator 400 has a reduced rotational inertia compared to a rotary gearbox.

Additionally, a motor and transmission with an overload protection system described herein may be coupled to the hip joint 403 to reduce the rotational inertia thereat. For instance, the motor and transmission may be installed along one or both of an x-axis 1100 and y-axis 1102 at the hip joint 403.

Figure 12A:
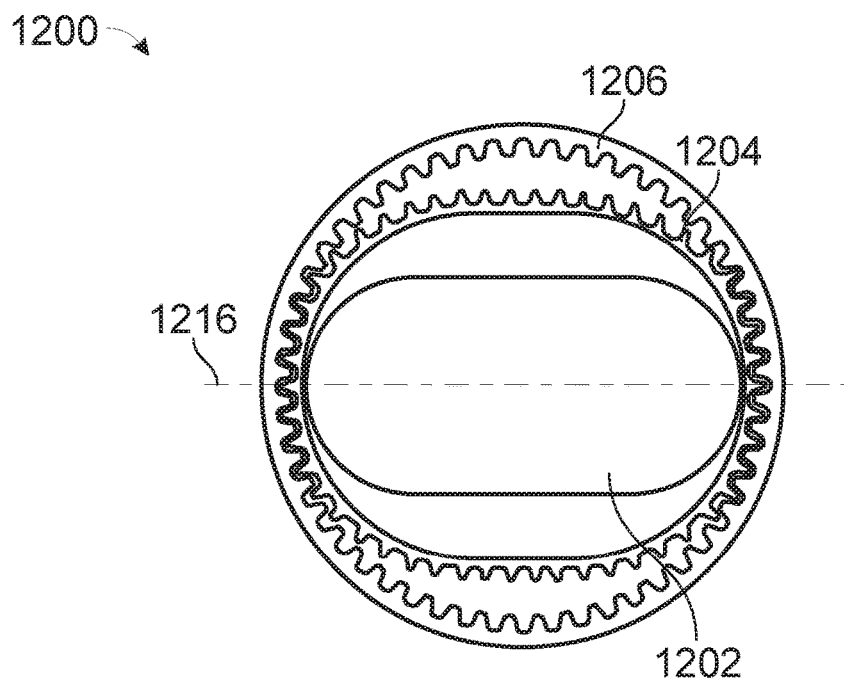
FIG. 12A illustrates a diagram showing operation of a harmonic drive, in accordance with an example implementation.
Figure 12B:
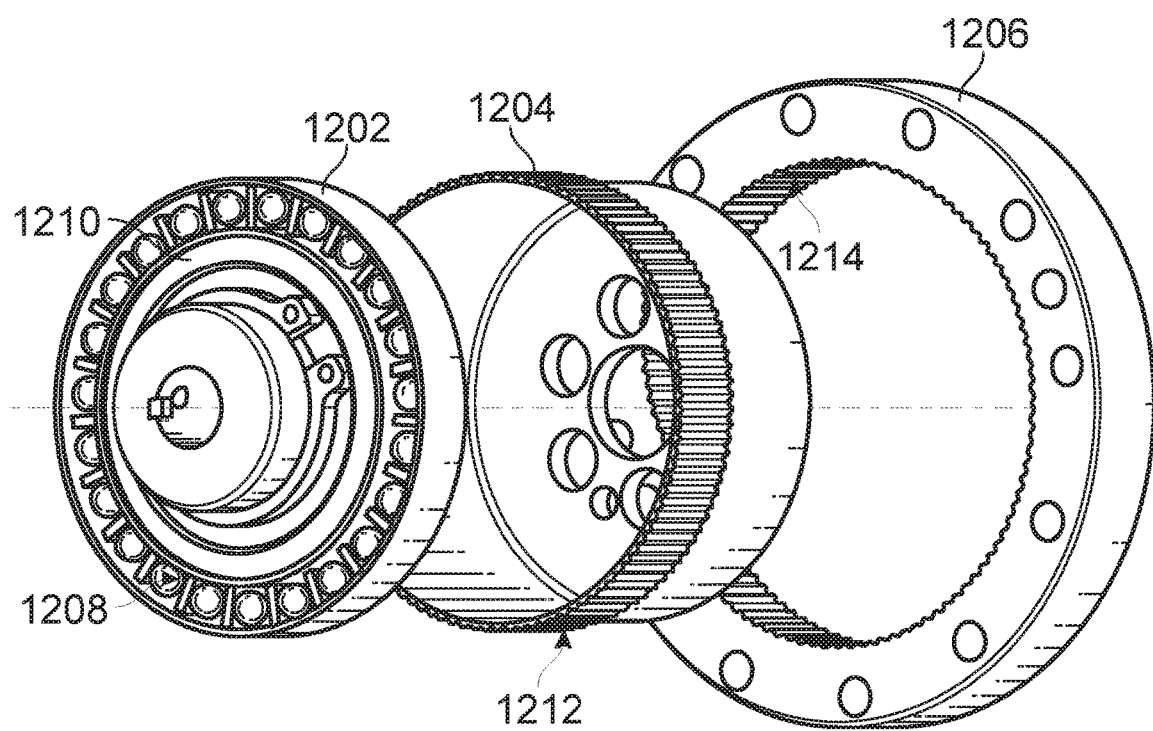
FIG. 12B illustrates an exploded view of the harmonic drive in FIG. 12A, in accordance with an example implementation.

FIG. 12A illustrates a diagram showing operation of a harmonic drive 1200, and FIG. 12B illustrates an exploded view of the harmonic drive 1200, in accordance with an example implementation. The harmonic drive 1200 is used herein as an example transmission system to operate as a speed reducer and torque amplifier. Harmonic drives are characterized by zero-backlash characteristics, a wide range of reduction ratios, weight and space savings compared to other transmission systems, high positional accuracy, and repeatability. However, other transmission systems, such as a cycloidal transmission, could be used.

As shown in FIG. 12A, the harmonic drive 1200 includes three main components: an input member that may be referred to as a wave generator 1202; an intermediate member that may be referred to as a flexspline 1204; and an outer member that may be referred to as a circular spline 1206. As illustrated in FIG. 12B, the wave generator 1202 may include a thin raced ball bearing 1208 that is fitted onto an elliptical hub 1210. The elliptical hub 1210 might not appear elliptical in FIG. 12B because the dimensional difference between the major and minor axes thereof is small. The wave generator 1202 operates as a torque converter and is connected to an input shaft from a motor, and thus operates as the input to the harmonic drive 1200.

The flexspline 1204 is a thin cylindrical cup made, for example, from alloy steel with external teeth 1212 on exterior peripheral surface of an open end of the cup. The flexspline 1204 is radially compliant or flexible, but is torsionally stiff. When the wave generator 1202 is inserted into the flexspline 1204, the wave generator 1202 interfaces with the external teeth 1212 of the flexspline 1204 at the open end thereof. Thus, the open end of the flexspline 1204 takes on the elliptical shape of the wave generator 1202.

The circular spline 1206 is a rigid ring with internal teeth 1214. When the harmonic drive 1200 is assembled, the internal teeth 1214 of the circular spline 1206 engage with the external teeth 1212 of the flexspline 1204 across a major axis 1216 of the elliptically shaped wave generator 1202. The circular spline 1206 may have more teeth than the flexspline 1204. For instance, the circular spline 1206 may have two more teeth than the flexspline 1204.

In examples, the flexspline 1204 is used as the output and may thus be connected to an output flange, whereas the circular spline 1206 is fixedly mounted. In other examples, the circular spline 1206 is used as the output and may thus be connected to an output flange, whereas the flexspline 1204 is fixedly mounted. In the example description provided below, the circular spline 1206 is allowed to rotate and may be connected to an output, whereas the flexspline 1204 is fixedly mounted. However, other configurations could be used.

When the elliptical hub 1210 of the wave generator 1202 is rotated, the flexspline 1204 deforms to the shape of elliptical hub 1210 and does not slip over the outer peripheral surface of the ball bearing 1208. As a result, the external teeth 1212 of the flexspline 1202 engage the internal teeth 1214 of the circular spline 1206 at two opposite regions across the major axis 1216 of the wave generator 1202. For every 180 degree rotation of the wave generator 1202, the internal teeth 1214 of the circular spline 1206 are advanced by one tooth in relation to the external teeth 1212 of the flexspline 1204. Thus, each complete rotation of the wave generator 1202 may result in the circular spline 1206 moving by two teeth from its original position relative to the flexspline 1204.

With a harmonic drive such as the harmonic drive 1200, a wide range of gear reduction ratios are possible in a small volume (e.g., a ratio from 30:1 up to 320:1). As mentioned above, having a low ratio may reduce reflected or output inertia of the transmission, i.e., the harmonic drive 1200, to facilitate high performance capabilities of the robot. To protect the harmonic drive 1200 in high impact situations, an overload protection system is integrated therein as described below.

Figure 13A:
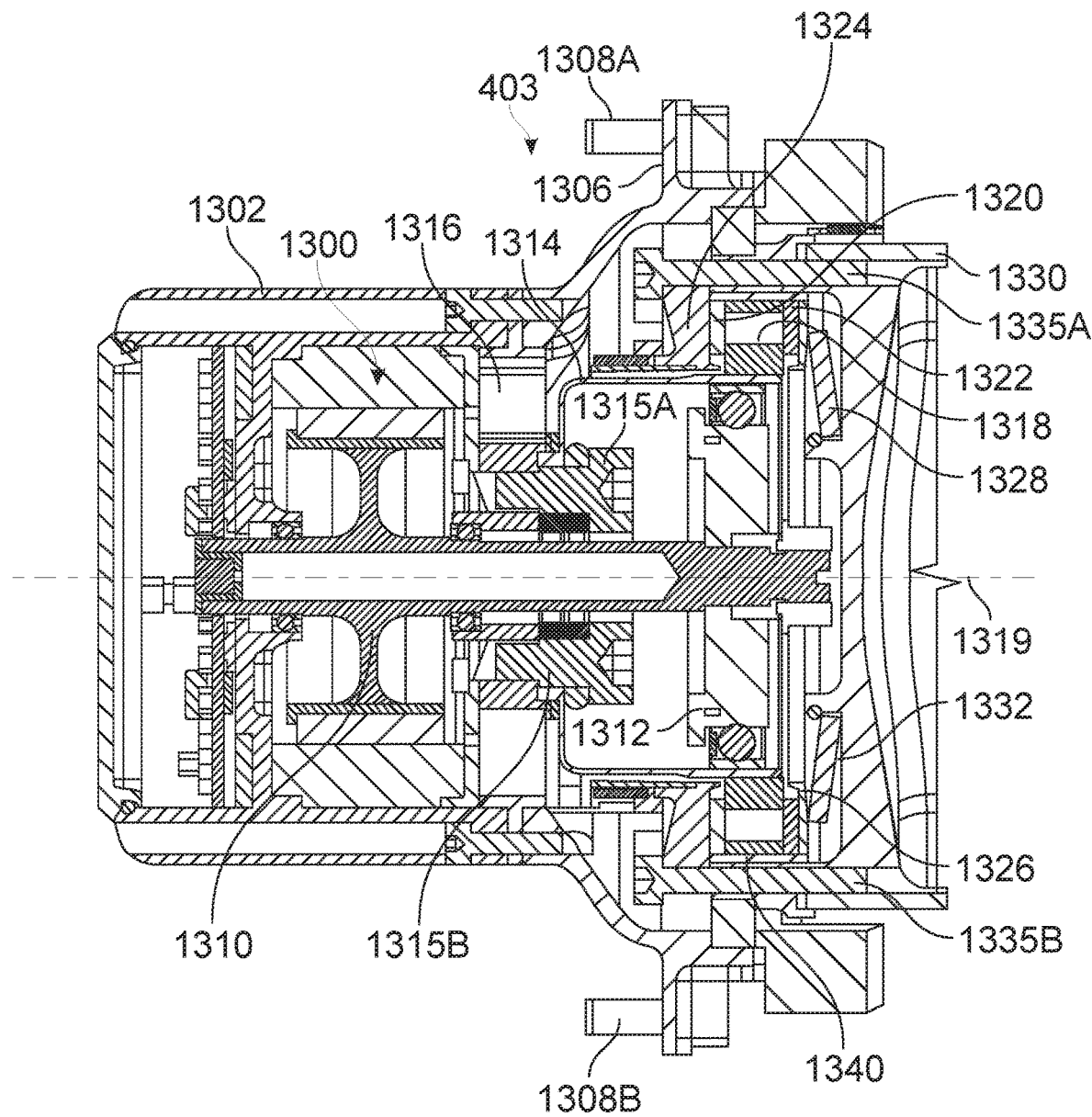
FIG. 13A illustrates an example drive system with integrated overload protection systems, in accordance with an example implementation.
Figure 13B:
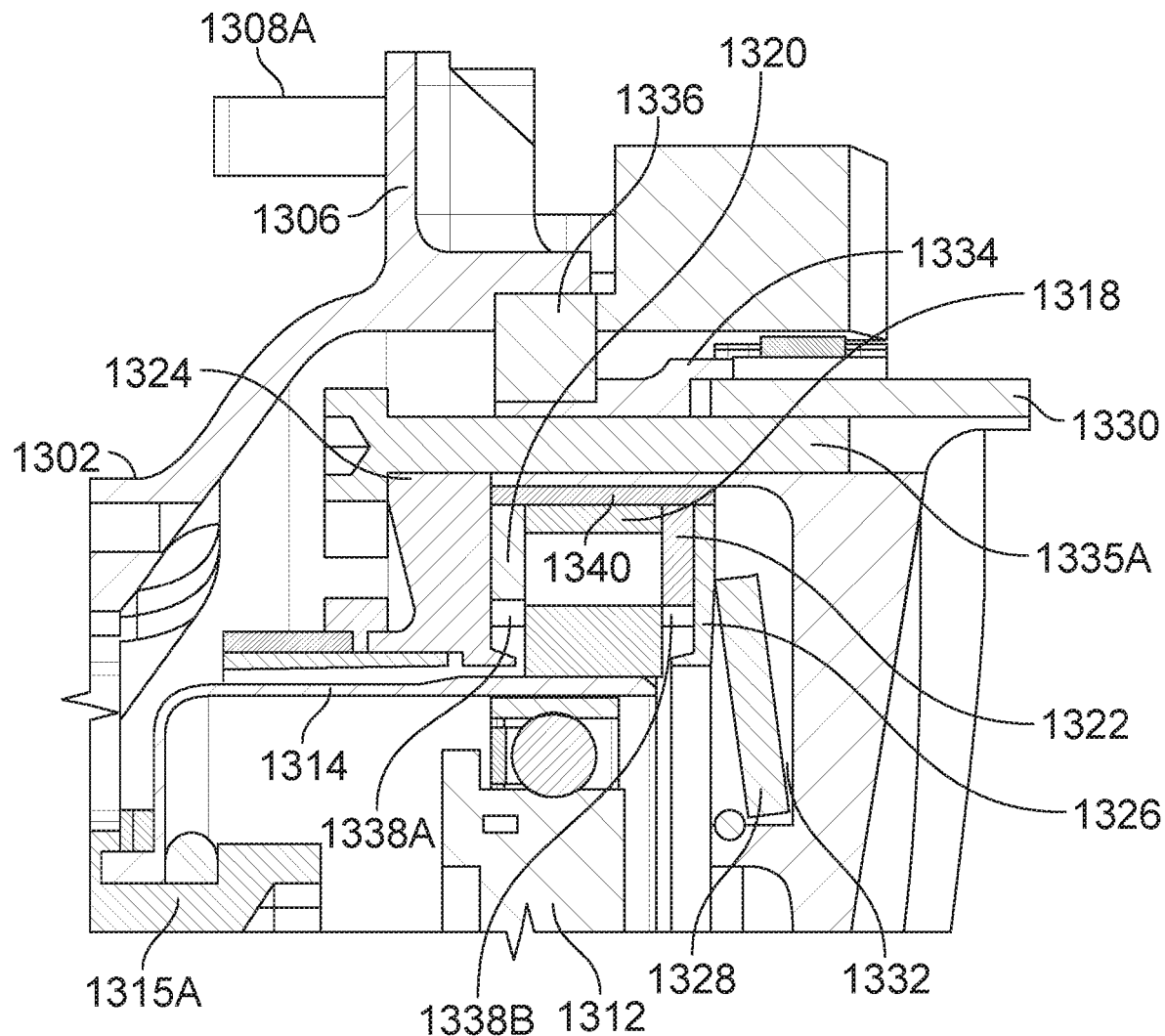
FIG. 13B illustrates a zoomed-in view of the drive system in FIG. 13A, in accordance with an example implementation.
Figure 13C:
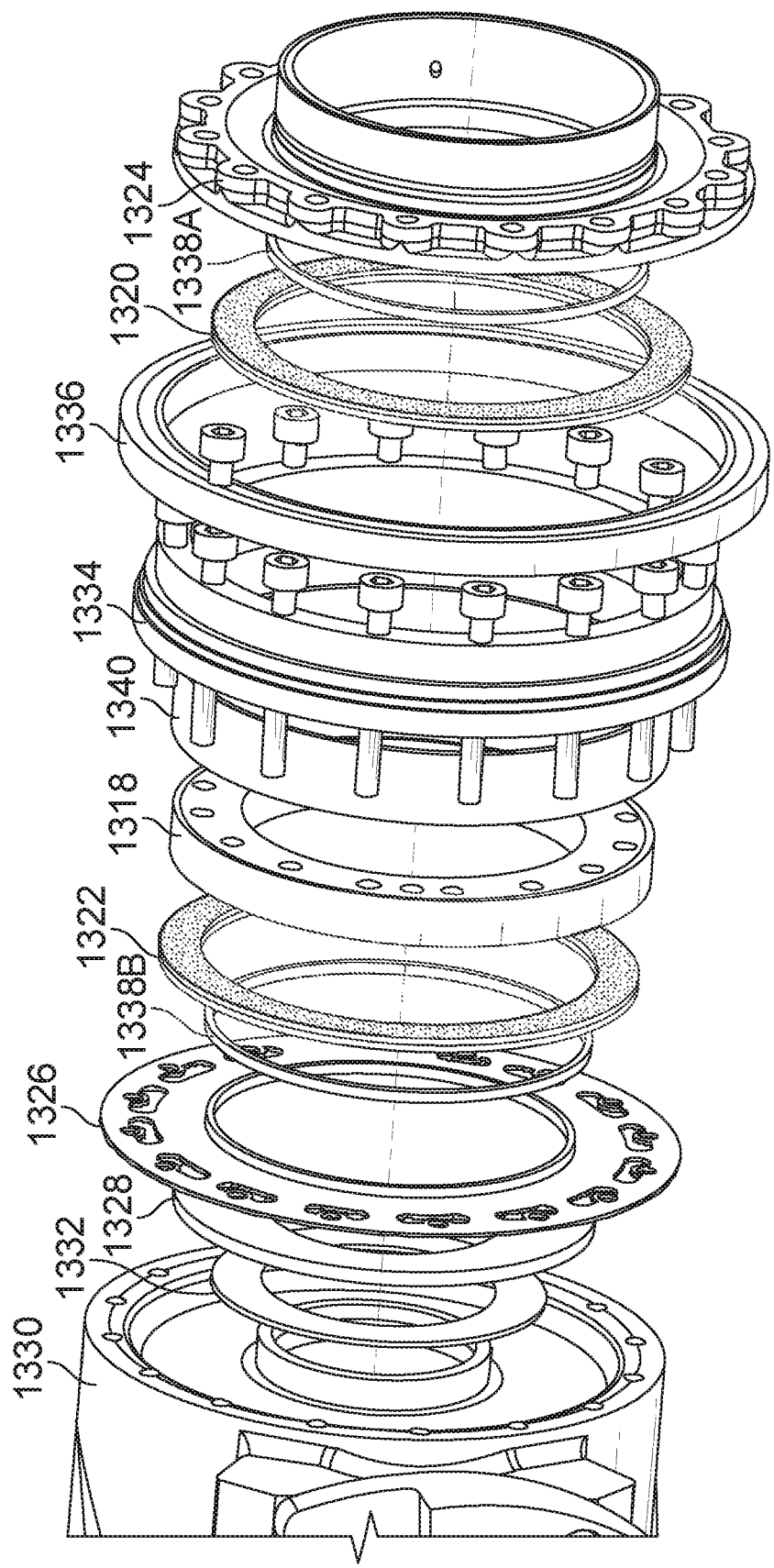
FIG. 13C illustrates an exploded view of the drive system in FIG. 13A, in accordance with an example implementation.

FIG. 13A illustrates an example drive system with integrated overload protection systems, FIG. 13B illustrates a zoomed-in view of the drive system in FIG. 13A, and FIG. 13C illustrates an exploded view of the drive system in FIG. 13A, in accordance with an example implementation. FIGS. 13A-13E are described together. The drive system in FIGS. 13A-13C could be coupled to either or both axes 1100 and 1102 of the hip joint 403, or any other joint of the robot. The description below refers to a motor and transmission at the hip joint 403 to drive a robot leg. However, the systems described herein could be used at any other joint to drive any other member (e.g., arms) of the robot.

A motor 1300 is mounted within a housing 1302 at the hip joint 403 of the robot. The housing 1302 is coupled to the robot via a flange 1306 and fasteners such as fasteners 1308A and 1308B.

A rotor of the motor 1300 is coupled to a shaft 1310 configured to rotate with the rotor. A wave generator 1312 that could be similar to the wave generator 1202 is coupled to and configured to rotate with the shaft 1310. The wave generator 1312 interfaces with a toothed portion of a flexspline 1314 that could be similar to the flexspline 1204. The flexspline 1314 is fixedly mounted via fasteners such as fasteners 1315A and 1315B to a load cell or torque sensor 1316, which in turn is fixedly mounted to the housing 1302. External teeth of the teethed portion of the flexspline 1314 engage with internal teeth of a circular spline 1318 that could be similar to the circular spline 1206. Teeth of the flexspline 1314 and the circular spline 1318 are not shown in FIGS. 13A-13C to reduce visual clutter in the drawings.

With this configuration, as the wave generator 1312 rotates with the shaft 1310, the circular spline 1318 rotates about a longitudinal axis 1319 because the flexspline 1314 is fixed. A proximal side surface of the circular spline 1318 interfaces with a first clutch pad 1320, and a distal side surface of the circular spline 1318 interfaces with a second clutch pad 1322. Herein, proximal side refers to the side closer to the motor 1300, and distal side refers to the side that is farther from the motor 1300.

The clutch pads 1320 and 1322 have friction material mounted to their surfaces that interface with respective surfaces of the circular spline 1318. Thus, as long as the clutch pads 1320 and 1322 are sufficiently preloaded against or biased toward the respective surfaces of the circular spline 1318, the clutch pads 1320 and 1322 rotate with the circular spline 1318.

The clutch pad 1320 also interfaces with and is coupled to a presser plate 1324. Similarly, the clutch pad 1322 also interfaces with and is coupled to an output flexure 1326. In an example, the clutch pad 1320 may be glued via any kind of adhesive to the presser plate 1324, and the clutch pad 1322 may be glued via any kind of adhesive to the output flexure 1326. Other fastening means could be used to couple the clutch pad 1320 to the presser plate 1324 and the clutch pad 1322 to the output flexure 1326. In an example, the presser plate 1324 could be made of aluminum. However, other materials are possible as well. Also, in another example, the clutch pads 1320 and 1322 may be glued to the circular spline 1318 and allowed to slide relative to the presser plate 1324 and the output flexure 1326. In still another example, the clutch pads 1320 and 1322 might not be glued to any other component and may be allowed to slide along any of the four surfaces, two surfaces for each clutch pad.

A Belleville spring 1328 is disposed between a robot member 1330 (e.g., a leg member) and the output flexure 1326. The Belleville spring 1328 exerts an axial biasing force on the output flexure 1326 so as to apply an axial preload on the clutch pad 1322. The axial preload on the clutch pad 1322 similarly preloads the clutch pad 1320 because the axial preload is transferred through the circular spline 1318 to the clutch pad 1320, which is constrained by the presser plate 1324.

The axial preload may keep the clutch pads 1320 and 1322 frictionally coupled to the circular spline 1318 until a predetermined torque limit is exceeded. If the torque limit is exceeded, the static friction limit of the clutch pads 1320 and 1322 may be exceeded, and the circular spline 1318 might slip relative to the clutch pads 1320 and 1322. Therefore, the torque limit may be referred to as the slip torque.

The torque limit is based on the spring rate of the Belleville spring 1328. Shims such as shim 1332 could be added between the Belleville spring 1328 and the robot member 1330 to vary the axial preload on the clutch pads 1320 and 1322 and thus vary the torque limit.

The output flexure 1326 may be torsionally stiff but axially flexible. For instance, the output flexure can be made of a flexible material such as titanium. In an example, the output flexure 1326 may be made of a softer material compared to the Belleville spring 1328. For instance, the output flexure 1326 may have a spring rate that is less than (e.g., 10%) of the spring rate of the Belleville spring 1328. In this example, the Belleville spring 1328 provides the dominant axial preload force compared to the force applied by the output flexure 1326 on the clutch pad 1322. However, other configurations are possible. The output flexure 1326 is configured to torsionally connect the robot member 1330 to the clutch pad 1322 while allowing axial motion thereof to accommodate wear and to also allow the Belleville spring 1328 to preload the clutch pad 1322 against the circular spline 1318.

In an example, a constraint ring 1334 may be disposed between the presser plate 1324 and the robot member 1330. The constraint ring 1334 has an open annular space in which the circular spline 1318 and the clutch pads 1320 and 1322 are disposed and constrained. In an example, the constraint ring 1334 may be made of aluminum; however, other materials are possible as well.

A radial array of fasteners or bolts, such as bolts 1335A and 1335B, may be configured to hold the assembly including the presser plate 1324, the constraint ring 1334, the output flexure 1326, and the robot member 1330 together. Due to the axial preload applied by the Belleville spring 1328, the clutch pads 1320 and 1322 and the circular spline 1318 are squeezed between the output flexure 1326 and the presser plate 1324. As such, the clutch pads 1320 and 1322 and the circular spline 1318 are also part of the assembly held together by the radial array of bolts including the bolts 1335A and 1335B

As mentioned above, as the wave generator 1312 rotates, the circular spline 1318 rotates because the flexspline 1314 is fixed. The circular spline 1318 rotates at a reduced rotational speed relative to the wave generator 1312 but can apply an amplified torque relative to the torque applied by the wave generator 1312. As the circular spline 1318 rotates, the clutch pads 1320 and 1322 frictionally coupled thereto also rotate, and the torque transferred from the circular spline 1318 to the clutch pads 1320 and 1322 is transferred to the robot member 1330 via two paths. The first path includes transferring the torque from the circular spline 1318 through the clutch pad 1322 to the output flexure 1326, which is coupled to the robot member 1330 via the array of bolts. The second path includes transferring the torque from the circular spline 1318 through the clutch pad 1320 to the presser plate 1324, which is coupled to the robot member 1330 via the array of bolts.

A cross roller bearing 1336 may be mounted to an external peripheral surface of the constraint ring 1334 between the constraint ring 1334 and an interior surface of the housing 1302. The cross roller bearing 1336 facilitates rotation of the robot member 1330 relative to the housing 1302 and may be configured to handle radial, thrust, and moment reaction loads applied to the robot member 1330.

The system described above facilitates overload protection of the motor 1302 and the harmonic drive while allowing for reducing speed reduction ratio of the harmonic drive, and thus reducing the rotational inertia thereof. As an example, the motor 1302 could be rotating fast to try to move the robot member 1330 to a particular location. As the robot member 1330 moves, it might hit or bump into an unexpected or undetected object. As a result, without an overload protection system, the motor 1302 may be forced to stop in a small period of time (e.g., 1 millisecond). A torque that may amount to four times the torque capacity of the harmonic drive may be applied thereto to stop it. If the harmonic drive is designed to be able to withstand or apply such a high torque, the harmonic drive would be larger and exhibit a larger rotational inertia.

As another example, the robot may impact an object, e.g., the robot may fall on a ground surface from a particular height, and the impact may cause a high torque to be applied to the harmonic drive that could cause damage. In another example, the robot may be in an inactive state (e.g., power to the robot via a battery for example is shut down, a cable is broken, or a controller malfunction occurred). If an object impacts the robot in such a state, the controller of the robot might not have power and might thus not send signals to electrically operated safety components to protect the robot. In all these examples, the harmonic drive and the motor 1302 may be subjected to a high torque that could cause damage to their components.

With the overload protection systems described in FIGS. 13A-13C, the circular spline 1318 would slip relative to the clutch pads 1320 and 1322 if the load torque on the robot member 1330 exceeds the torque limit specified by the axial preload of the Belleville spring 1332. In this manner, the harmonic drive (i.e., the circular spline 1318) is decoupled for a period of time from the robot member 1330 and is thus protected from the high load torque. Further, as the circular spline 1318 slips relative to the clutch pads 1320 and 1322, kinetic energy of the robot member 1330 is dissipated due to the friction between the circular spline 1318 and the clutch pads 1320 and 1322. Once the load torque falls back below the torque limit, the harmonic drive reengages with the robot member 1330.

An advantage of the overload protection system is that the clutch pads 1320 and 1320 are integrated within the harmonic drive and interface with the components thereof (i.e., the circular spline 1318). This integration allows for a compact design as opposed to adding a clutch system inline with the harmonic drive, which would require more longitudinal space.

Another advantage is that the output flexure 1326 is configured to allow the robot member 1330 to reverse its direction of motion with zero backlash. Most robot members such as the robot member 1330 operate in two directions. For instance, if the robot member 1330 is a leg of the robot, the motor 1302 may spin in one direction to swing the leg in a corresponding direction, then stop the leg and spin in a reverse direction to swing the leg in an opposite direction. Accurate control of position, speed, and acceleration of the leg in addition to control of the force applied by the leg may depend on several factors including zero backlash when reversing the direction of motion.

If there is backlash, then one clutch pad of the two clutch pads 1320 and 1322 may be engaged with the circular spline 1318 upon reversing direction while the other clutch pad might not be engaged. Thus, the engaged clutch pad may start to slip relative to the circular spline 1318 and then after a period of time, the other clutch pad may start to be loaded, and then both clutch pads 1320 and 1322 would slip together relative to the circular spline 1318.

Because of the flexibility of the output flexure 1326 and Belleville spring 1328, they can accommodate axial movement of components of the drive system relative to each other. For example, they can accommodate wear in the clutch pads 1320 and 1322, axial movement of the robot member 1330 relative to the harmonic drive, etc. without overstressing the components. Thus, the output flexure 1326 and the Belleville spring 1328 can compensate for manufacturing tolerance of the various components.

At the same time, the output flexure 1326 pushes against the clutch pad 1322 and causes the clutch pads 1320 and 1322 to remain in contact with the circular spline 1318, thus eliminating backlash. Therefore, even if the motor 1302 and the circular spline 1318 stop and then their direction of rotation is reversed, the output flexure 1326 may ensure smooth movement of the robot member 1330.

Further, the output flexure 1326 may cause the torque load to be equally shared between the two clutch pads 1320 and 1322. The force applied by the output flexure 1326 maintains contact between the clutch pad 1322 against the circular spline 1318. The same force applied by the output flexure 1326 further squeezes the clutch pad 1322 against the circular spline 1318 along with the clutch pad 1320 against the presser plate 1324. This way, the clutch pads 1320 and 1322 are equally loaded as the circular spline 1318 rotates.

In some examples, grease or other lubricants could be applied to components of the harmonic drive or bearings in the drive system illustrated in FIGS. 12A-13B. Lubricants reduce wear of, and friction between, the meshing components of the drive system. In these examples, seals such as O-rings 1338A and 1338B could be used to keep grease away from the clutch pads 1320 and 1322. Particularly, the O-ring 1338A could keep the grease away from the clutching interface between the clutch pad 1320 and the proximal face of the circular spline 1318. And, the O-ring 1338B could keep the grease away from the clutching interface between the clutch pad 1322 and the distal face of the circular spline 1318. This way, the grease might not affect the torque limit (i.e., the slip torque) determined at least partially by the spring rate of the Belleville spring 1328.

However, in other example implementations, the O-rings 1338A and 1338B might not be used. The axial preload imposed by the Belleville spring 1328 may then be adjusted, e.g., by choosing a Belleville spring with a different spring rate, to accommodate the presence of grease. Changing the spring rate of the Belleville spring may tune performance of the clutch pads 1320 and 1322 to operate at a reduced coefficient of friction resulting from the presence of grease.

As mentioned above, as the wave generator 1312 rotates with the shaft 1310 of the motor 1302, the circular spline 1318 also rotates due to the flexspline 1314 being fixed. As the circular spline 1318 rotates, the assembly including the clutch pads 1320-1322, the presser plate 1324, and the constraint ring 1334 also rotates. The robot member 1330 also rotates via the radial array of bolts (e.g., the bolts 1335A-1335B). As long as the load torque applied to the robot member 1330 does not exceed the torque limit, the assembly and the robot member 1330 rotate with the circular spline 1318. If the load torque exceeds the torque limit, the circular spline 1318 slips relative to the clutch pads 1320 and 1320.

In a torque overload situation, the oval shape of the wave generator 1312 may distort the circular spline 1318 into an oval shape as well. When the torque falls back below torque limit, the clutch pad 1320 and 1322 reengage the circular spline 1318, and may thus cause its shape to remain ovalized. Such a distorted oval shape of the circular spline 1318 may result in torque pulsations at the robot member 1330.

To preclude keeping the circular spline 1318 in a distorted shape state, a constraint bushing 1340 may be inserted between an external peripheral surface of the circular spline 1318 and an internal peripheral surface of the constraint ring 1334. The clearance between the external peripheral surface of the circular spline 1318 and the internal peripheral surface of the constraint ring 1334, and thus the thickness of the constraint bushing 1340, is small. For instance, the interference could be 1/1000th of an inch.

In examples, the constraint bushing 1340 may be made of a plastic material, e.g., Polyether ether ketone (PEEK) material or other polymeric material. Plasticity of the constraint bushing 1340 imparts a relatively low stiffness thereto, thus facilitating insertion of the constraint busing 1340 with a light press fit in the interference. This configuration accommodates production variations in dimensions and concentricity of the circular spline 1318 and the constraint ring 1334.

During operation of the robot, respective temperatures of the constraint bushing 1340, the circular spline 1318, and the constraint ring 1334 may rise. The circular spline 1318 and the constraint ring 1334 may expand and contract at different rates because they could be made of different material having different coefficients of thermal expansion. However, the plastic material of the constraint bushing 1340 may become softer, and thus accommodate any dimensional variations in the circular spline 1318 and the constraint ring 1334 due to temperature changes.

Further, the constraint bushing 1340 couples the circular spline 1318 and the constraint ring 1334 such that they move as one assembly. Thus, when a shape of the circular spline 1318 changes (e.g., ovalized) under torque load, the circular spline 1318 and the constraint ring 1334 may be distorted together along with the constraint bushing 1340. This way, when the torque load falls back below the torque limit, the circular spline 1318, the constraint bushing 1340, and the constraint ring 1334 may spring back together to an undistorted shape. Also, the circular spline 1318, the constraint bushing 1340, and the constraint ring 1334 may deform less because of the presence of the constraint bushing 1340 as opposed to having a gap or clearance. Thus, the presence of the constraint bushing 1340 may prevent torque pulsations.

The circular spline 1318 and the constraint ring 1334 could be made of different materials. For instance, the circular spline 1318 could be made of cast iron, while the constraint ring 1334 may be made of titanium. Allowing the circular spline 1318 to be in contact with the constraint ring 1334 might cause binding and galling therebetween. The constraint bushing 1340 operates as an interface between the circular spline 1318 and the constraint ring 1334 to preclude such binding and galling, while preventing torque pulsations as described above.

The components and configurations described above with respect to FIGS. 12A-13C are example components and configurations and are not meant to be limiting. Other components and configurations could be used. For example, instead of using two clutch pads, one clutch pad may be used. In another example, a clutch pad may be used on one side of the circular spline 1318, and any type of friction material including bare metal on metal contact could be used on the other side thereof.

In the configuration described above, the overload protective clutching operation takes place on the interface between the clutch pads 1320 and 1322 and the circular spline 1318. In another example implementation, the clutching operation could take place on the interface between the clutch pad 1320 and the output flexure 1326 and between the clutch pad 1322 and the presser plate 1324. In this example, the clutch pads 1320 and 1320 may be integrated with the circular spline 1318. In other words, the proximal and distal faces of the circular spline could have friction material disposed thereon. Further, in other examples, other components may be added between the circular spline 1318 and the clutch pads 1320 and 1322. In another example variation, the output flexure 1404 and the Belleville spring 1328 may be integrated into one flexible component. Also, a Belleville spring is used herein as an example, and in other implementations any other type of springs or flexible, compliant elements could be used.

Figure 14:
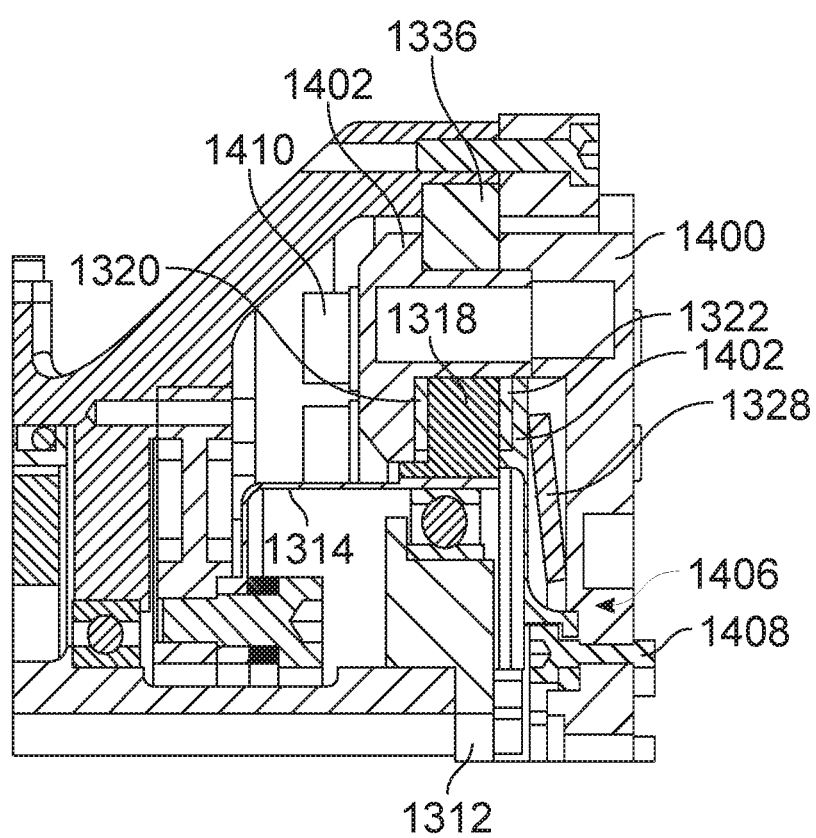
FIG. 14 illustrates an alternative configuration for a drive system of a robot member, in accordance with an example implementation.

FIG. 14 illustrates an alternative configuration for a drive system of a robot member 1400, in accordance with an example implementation. As shown in FIG. 14, a bolt ring 1402 replaces the presser plate 1324 and the constraint ring 1334. In other words, the presser plate 1324 and the constraint ring 1334 can be integrated into a single component shown as the bolt ring 1402 in FIG. 14.

An output flexure 1404, which may perform similar operations as the output flexure 1326, is coupled to the robot member 1400 at a central region 1406 via a bolt array including bolts such as bolt 1408. In contrast to the bolts 1335A-1335B, bolts such as bolt 1410 in FIG. 14 couple the bolt ring 1402 to the robot member 1400 without coupling the output flexure 1402 thereto.

These variations are examples for illustration only, and those skilled in the art will appreciate that other arrangements and other elements (e.g., components, interfaces, orders, and groupings of components, etc.) can be used instead, and some elements may be omitted altogether according to the desired results.

c. Example Motor-Controller Integration Configuration

An example robot may include several joints to control motion of corresponding members of the robot. As an example, a quadruped robot may have 17 joints that connect and control the members of the robot (e.g., arms, legs, etc.). In examples, many of these joints may have respective motors configured to move the members of the robot. Each of the motors is controlled by a controller that receives several inputs (e.g., from sensors) and accordingly provide control signals to the motor to control the joint and members of the robot.

In an example, a controller may be placed at a central location on the robot and wires could be connected between the controller and the various motors and sensors. This configuration may involve complex wiring and long wires that may reduce the reliability of the robot and increase the probability of failure.

In other examples, each joint may have a respective motor and a controller for that motor. Integrating and co-locating the motor and its controller may improve the reliability of the robot. Such integration may reduce the complexity of the wiring configuration.

Disclosed herein are systems and apparatuses having integrated motor and controller assemblies to reduce complexity of the robot and increase reliability. Particularly, a motor and its controller may be integrated into a compact package proximate to each other to facilitate sharing sensors and thermal management components. With the configurations disclosed herein, the number and lengths of wires are reduced, thus enhancing the reliability of the robot by reducing points of potential failure. These configurations may thus reduce the likelihood of failure and downtime for the robot and lower the maintenance cost of the robot.

Figure 15A:
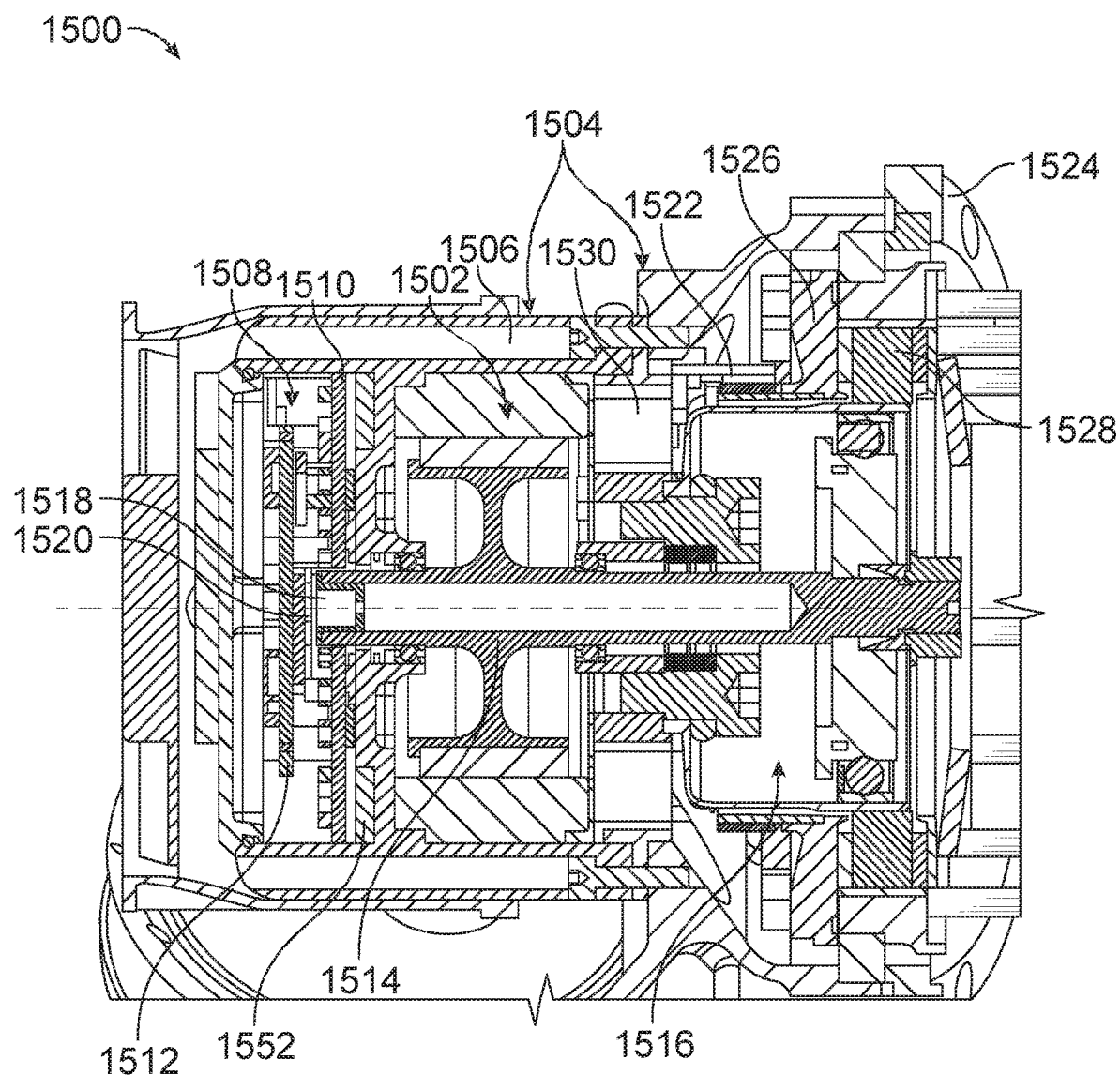
FIG. 15A illustrates an integrated motor controller assembly, in accordance with an example implementation.

FIG. 15A illustrates an integrated motor controller assembly 1500, in accordance with an example implementation. As shown, the assembly 1500 includes a motor 1502 disposed within a housing 1504. The housing 1504 includes heatsink fins 1506 that are circumferentially spaced apart in a circular array about an exterior surface of the housing 1504.

The assembly 1500 includes a controller 1508 that may include one or more printed circuit board (PCBs). For example, the controller 1508 may include a power stage PCB 1510 and a logic stage PCB 1512. The power stage PCB 1510 may for example include the power electronics that might include solid-state electronics configured for the control and conversion of electric power provided to the windings of a stator of the motor 1502. For instance, the power stage PCB 1510 may include a plurality of field-effect transistors (FETs).

The logic stage PCB 1512 may, for example, include one or more microprocessors and data storage including instructions to be executed by the one or more microprocessors to perform various control operations for the motor 1502. The power stage PCB 1510 and logic stage PCB 1512 are in communication with each other. In the example implementation shown in FIG. 15A, the power stage PCB 1510 and logic stage PCB 1512 are juxtaposed or arranged on respective axially spaced planes. In other examples, however, they may be disposed in a different configuration and in some examples components of the power stage PCB 1510 and components of the logic stage PCB 1512 may be integrated into a single PCB.

The rotor of the motor 1502 is coupled to a shaft 1514 that transmits the rotary motion of the rotor to a transmission such as a harmonic drive 1516. In an example, the shaft 1514 may be hollow and a magnet 1518 may be disposed at a proximal end therein. Herein, the term "proximal end" refers to the end of the shaft 1514 that is closer to the controller 1508, whereas a "distal end" of the shaft 1514 refers to the end that is coupled to the harmonic drive 1516.

As shown, the shaft 1514 extends through the power stage PCB 1510 such that the magnet 1518 is disposed closer to and facing the logic stage PCB 1512. Further, the logic stage PCB 1512 may include a rotary position sensor 1520 (e.g., a magnetoresistive or Hall Effect sensor) disposed thereon facing the magnet 1518.

The magnet 1518 may be diametrically magnetized such that as the shaft 1514 and the magnet 1518 coupled thereto rotate, the sensor 1520 provides information indicative of the rotary position of the shaft 1514 to the controller 1508. This information is used by the controller 1508 to control commutation of the motor 1502. With this configuration, the rotary position sensor 1520 of the motor 1502 is integrated into the motor controller 1508. This configuration contrasts with other configurations where a rotary position sensor of a motor is disposed closer to the motor and wires connect the sensor with the controller, thus increasing the likelihood of wire breakage and failure.

The assembly 1500 may further include another rotary position sensor or output encoder 1522 configured to provide information indicative of the rotary position of a robot member 1524 to the logic stage PCB 1512. For instance, the output encoder 1522 may be coupled to a presser plate 1526, which may be coupled to the robot member 1524. By measuring the rotary position of the presser plate 1526, the output encoder 1522 provides measurements of the rotary position of the robot member 1524.

In this manner, the controller 1508 receives information indicating the rotary positions of the motor 1502 and the robot member 1524. As such, the controller 1508 may determine whether a circular spline 1528 of the harmonic drive 1516 slipped due to overloading as described above with respect to FIGS. 13A-14. The assembly 1500 further includes a torque load cell or torque sensor 1530 configured to measure the torque load on the harmonic drive 1516.

Figure 15B:
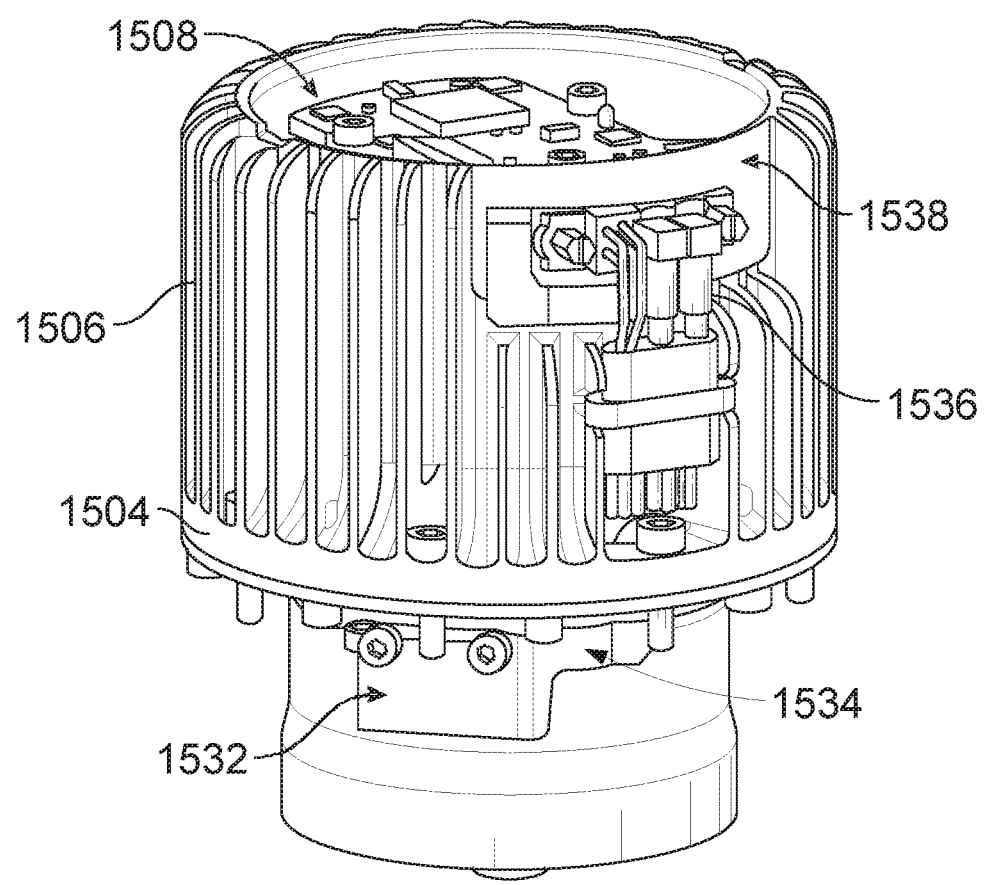
FIG. 15B illustrates connecting a torque sensor and an output encoder to a controller, in accordance with an example implementation.

FIG. 15B illustrates connecting the torque sensor 1530 and the output encoder 1522 to the controller 1508, in accordance with an example implementation. Wires from the torque sensor 1530 and the output encoder 1522 may be routed to and combined at a connection 1532 fixed to the torque sensor 1530, which is fixed to housing of the stator of the motor 1502. The wires may then be connected to a flexible PCB 1534 that might be configured to perform preliminary processing on the signals from the torque sensor 1530 and the output encoder 1522 (e.g., signal amplification, filtering, etc.).

Wires from the flexible PCB 1534 may then be routed through the housing 1504 to one or more connectors 1536. The connectors 1536 may be configured to mate with corresponding connectors 1537 (shown in FIGS. 15D and 15G) coupled to the controller 1508 (e.g., to the power stage PCB 1510) through a sealing grommet 1538. With this configuration, having the output encoder 1522 and the torque sensor 1530 close to the controller 1508 facilitates integration and shortening the wires, thus improving reliability of the robot.

Figure 15C:
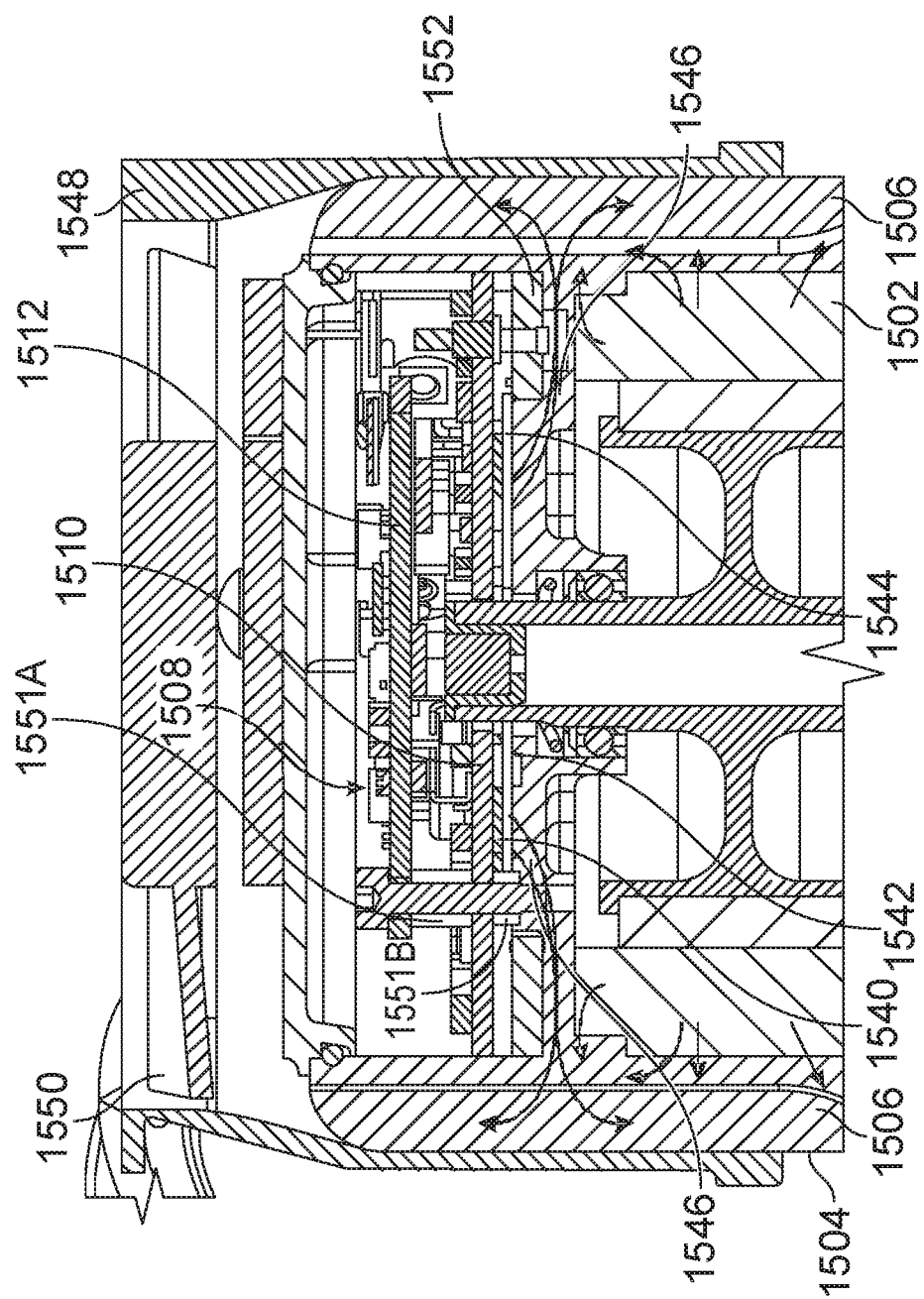
FIG. 15C illustrates thermal management of the assembly shown in FIG. 15A, in accordance with an example implementation.
Figure 15D:
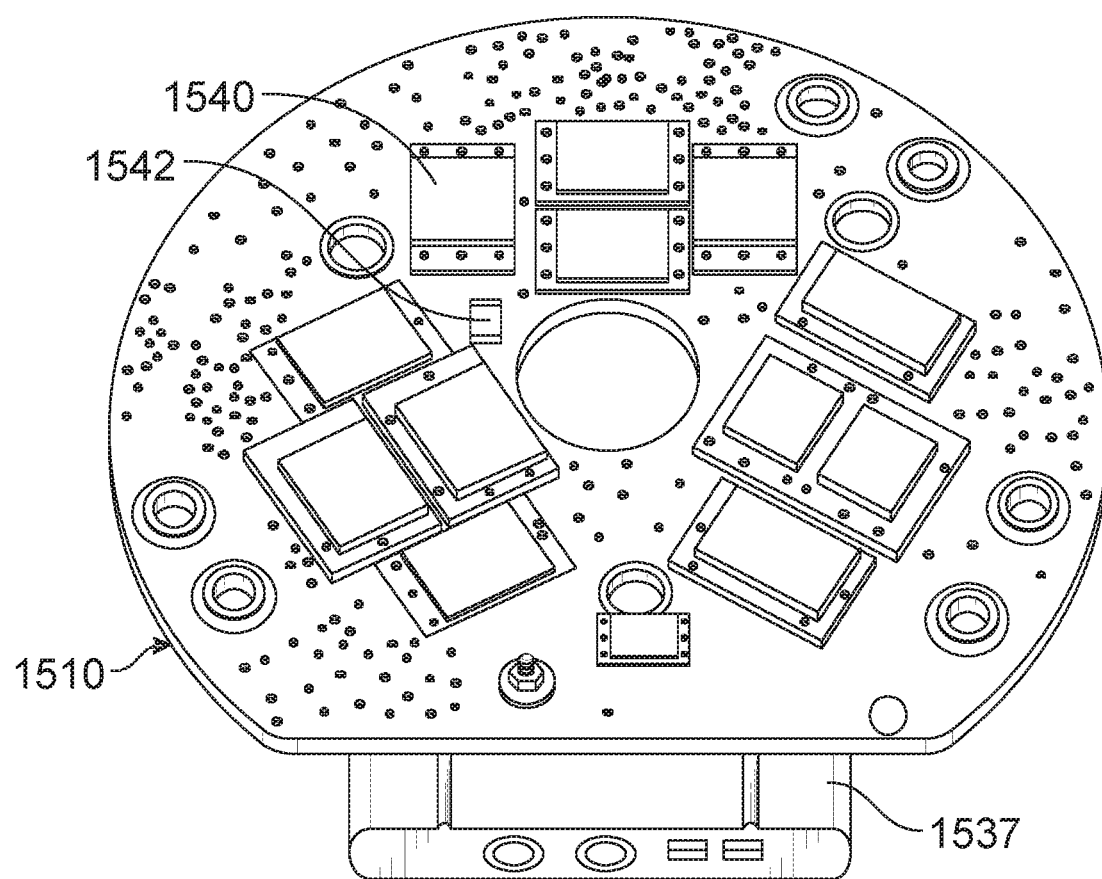
FIG. 15D illustrates a bottom view of a power stage printed circuit board, in accordance with an example implementation.

The configuration shown in FIGS. 15A-15B may also allow for sharing thermal management components between the motor 1502 and the controller 1508. FIG. 15C illustrates thermal management of the assembly 1500, and FIG. 15D illustrates a bottom view of the power stage PCB 1510, in accordance with an example implementation.

FETs 1540 may be disposed on a surface of the power stage PCB 1510 that faces away from the logic stage PCB 1512. Also, a thermal sensor 1542 is disposed on the same surface of the power stage PCB 1510 having the FETs 1540 disposed thereon. A thermal interfacial material 1544 separates the power stage PCB 1510 and the components mounted thereon (e.g., the FETs 1540 and the thermal sensor 1542) from ribs 1546 that protrude radially inward from an interior peripheral surface of the housing 1504. In other example implementations, any other thermal coupling surfaces or thermally conductive structures could be used instead of or in addition to the ribs 1546. For instance, instead of distinct ribs, a solid surface could be used. Other examples are possible.

The thermal interfacial material 1544 could be a flexible, compliant material that can compensate for height variations of components mounted on the power stage PCB 1510. The thermal interfacial material 1544 includes thermally conductive materials, which may increase thermal contact conductance across jointed solid surfaces in order to increase thermal transfer efficiency. Rather than leaving the gaps between the power stage PCB 1510 and the ribs 1546 filled with air, which is a poor thermal conductor, the thermal interfacial material 1544 provides for an enhanced thermal efficiency and transfer. Particularly, thermal transfer between the power stage PCB 1510 and the ribs 1546 is enhanced.

The thermal interfacial material 1544 may include a silicon based material or a non-silicon based material and may take several forms. For instance, the thermal interfacial material 1544 may include a paste or thermal grease made, for example, of silicone oil filled with aluminum oxide, zinc oxide, or boron nitride. The thermal interfacial material 1544 may also use micronized or pulverized silver. In examples, the thermal interfacial material 1544 may include fiberglass for reinforcement.

The ribs 1546 are configured to also provide a heat path for the heat generated by the motor 1502, and particularly by its stator windings. With this configuration, the controller 1508 and the motor 1502 share a common thermal management and dissipation arrangement. The arrows in FIG. 15D illustrate example heat paths for both the motor 1502 and the controller 1508. Heat generated from the motor 1502 and the controller 1508 is conducted through the ribs 1546 to the fins 1506 disposed on the housing 1504.

A shroud 1548 encloses a fan 1550 that, when activated, draws air and directs the air toward the fins 1506. In this manner, the fan 1550 may enhance heat dissipation at the fins 1506 and cool both the motor 1502 and the controller 1508.

The thermal sensor 1542 is placed on the power stage PCB 1510 on the same surface having the FETs 1540 as mentioned above, and thus provides information indicative of the temperature of the FETs 1540 and other components of the controller 1508. The thermal sensor 1542 may also be in contact with or proximate to the ribs 1546. The thermal sensor 1542 may thus also provide information indicative of the temperature of the stator of the motor 1502, which is adjacent to the ribs 1546. With this configuration, both the motor 1502 and the controller 1508 share a common thermal sensor. The sensor information provided by the thermal sensor 1542 to the controller 1508 may be used to control when to operate the fan 1550 and at what speed.

The thermal sensor 1542 may also be used for safety monitoring of the motor 1502 and the harmonic drive 1516 (shown in FIG. 15A). For instance, the thermal sensor 1542 may indicate that the temperature of the stator exceeds a threshold temperature, which may in turn indicate that the motor 1502 or the harmonic drive 1516 is overloaded. Alternatively, the high temperature may indicate that components of the harmonic drive 1516 might be misaligned and that maintenance may be due.

In this manner, the thermal sensor 1542 may indicate to the controller 1508 the state of the various components of the controller 1508 itself and the motor 1502. The controller 1508 may then determine whether to continue operation of the joint or shut it down for safety reasons. Thus, integrating the motor 1502 and the controller 1508 as shown in FIGS. 15A-15D allows for having a common thermal sensor for both of them, thereby reducing the lengths and extent of wiring associated with thermal management.

If the motor 1502 and the controller 1508 each has its own thermal sensor, then double the number of sensors and wiring would be added to the robot. For a quadruped robot that has 17 joints, the amount and extent of wiring increases significantly, thus reducing reliability of the robot as a whole. Integration leads to reduction in component count and wiring complexity, which may have enhance overall reliability of the robot.

In examples, as shown in FIG. 15C, logic stage stand-offs such as stand-off 1551A could be used to provide for a consistent distance between the logic stage PCB 1512 and the power stage PCB 1510. These stand-offs may ensure that components of both PCBs do not touch each other.

Further, power stage stand-offs such as stand-off 1551B could be used to provide for a consistent gap or distance between the FETs 1540 and the ribs 1546. The FETs 1540 could be "live" and thus may have a high voltage that could damage other components if conducted thereto. The power stage stand-offs preclude the FETs 1540 from contacting any other components. Further, providing a consistent distance between the FETs 1540 and the ribs 1546 facilitates estimating the amount and thickness of the thermal interfacial material 1544 to be disposed therebetween.

In examples, the motor 1502 may be a three-phase motor that has three windings or phases positioned 120 □ electrically apart. The stator of the motor 1502 may include 12 slots windings, and may thus have 12 wires coming out thereof. These 12 wires can be arranged into several configurations such as delta, star, parallel, or series configurations. The configuration may affect the performance and torque output of the motor 1502.

Although 12 wires come out of the stator, after configuring the wires into a star, parallel, or series configuration, the number of wires is reduced to 3 or 6 wires to be received at the controller 1508. To facilitate the interface between the 12 wires coming out of the stator and the controller 1508, a phase board 1552 may be disposed therebetween. The phase board 1552 operates as an intermediate or transition board between the stator of the motor 1502 and the controller 1508.

Figure 15E:
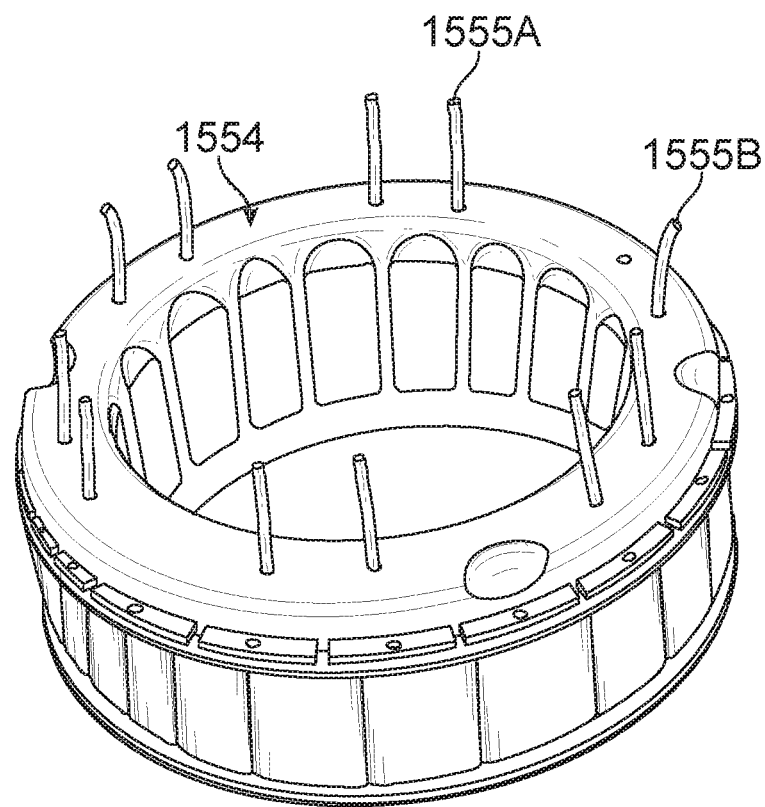
FIG. 15E illustrates 12 wires emanating from a stator of a motor, in accordance with an example implementation.
Figure 15F:
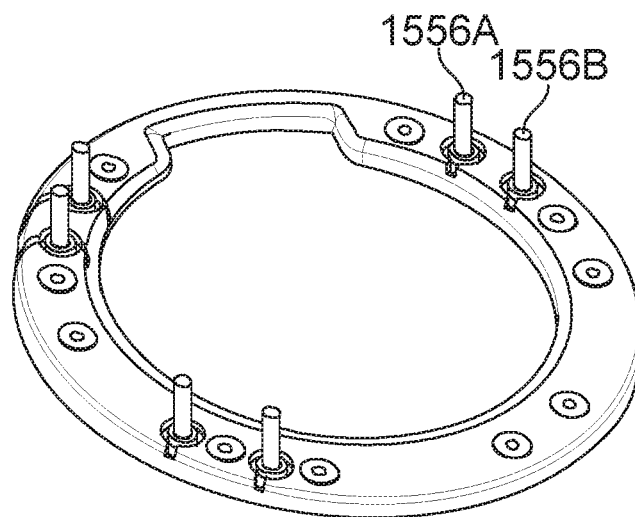
FIG. 15F illustrates a phase board configured to interface with a stator, in accordance with an example implementation.

FIG. 15E illustrates 12 wires emanating from a stator 1554 of the motor 1502, and FIG. 15F illustrates the phase board 1552 configured to interface with the stator 1554, in accordance with an example implementation. The stator 1554 presents 12 individual winding wires such as wires 1555A and 1555B. The phase board 1552 is configured to receive the 12 wires from the stator 1554 and includes conductive lines therein that make the final connection into star, delta, parallel, or series desired configuration. The phase board 1552 then presents 3 or 6 pins such as pins 1556A and 1556B to the controller 1508, i.e., to the power stage PCB 1510. With this configuration, the phase board 1552 transitions the wires coming out of the stator 1554 into robust pins to be received at connectors of the power stage PCB 1510. This configuration reduces wiring complexity and increases reliability and enhances the ability to repair the assembly 1500.

In examples, the phase board 1552 may be coupled (e.g., glued via any type of adhesive) to the stator 1554. To change the wiring configuration (e.g., from star to delta), the phase board 1552 may be removed and a different phase board that realizes the desired wiring configuration may be coupled to the stator 1554 without changes to the stator 1554. In this manner, minimal changes are performed on the stator 1554, and the risk of damaging the stator 1554 is reduced.

Similarly, no changes or minimal changes are performed to the controller 1508. The replacement phase board would provide the same number of pins to the controller 1508. In this manner, the risk of damaging the controller 1508, which could be expensive, is reduced.

Figure 15G:
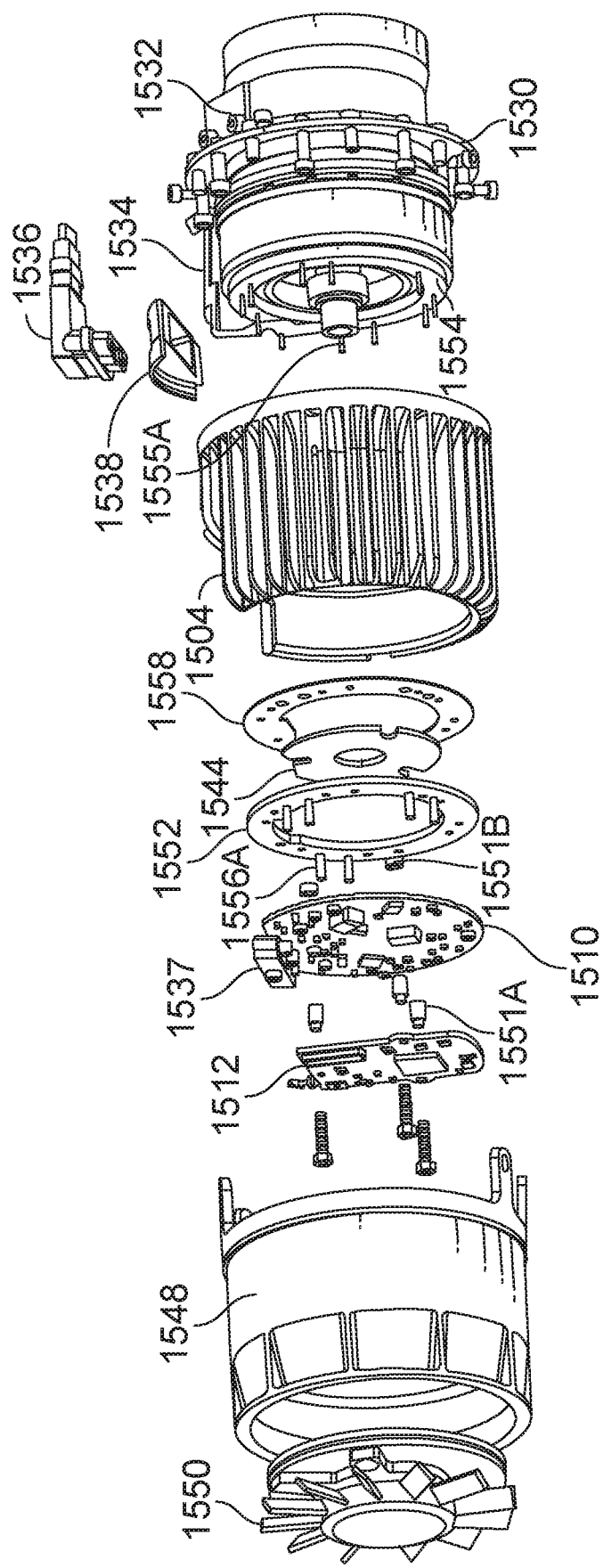
FIG. 15G illustrates an exploded view of the assembly shown in FIG. 15A, in accordance with an example implementation.

FIG. 15G illustrates an exploded view of the assembly 1500, in accordance with an example implementation. The exploded view in FIG. 15G further illustrates the relationship and order of assembly of various components of the assembly 1500. In an example, as shown in FIG. 15G, an electric insulation sheet 1558 could be disposed between the phase board 1552 and the housing 1504 to ensure electric insulation therebetween.

As such, the integration the motor 1502 and the controller 1508 and sharing of components allows for reducing the size and complexity of the assembly 1500. Further, the likelihood of wire damage is reduced, and reliability of the assembly 1500 is increased. The increase in reliability is magnified for the robot as a whole given that the robot may include many assemblies similar to the assembly 1500.

III. CONCLUSION

The arrangements described herein are for purposes of example only. As such, those skilled in the art will appreciate that other arrangements and other elements (e.g., machines, interfaces, operations, orders, and groupings of operations, etc.) can be used instead, and some elements may be omitted altogether according to the desired results. Further, many of the elements that are described are functional entities that may be implemented as discrete or distributed components or in conjunction with other components, in any suitable combination and location.

While various aspects and implementations have been disclosed herein, other aspects and implementations will be apparent to those skilled in the art. The various aspects and implementations disclosed herein are for purposes of illustration and are not intended to be limiting, with the true scope being indicated by the following claims, along with the full scope of equivalents to which such claims are entitled. Also, the terminology used herein is for the purpose of describing particular implementations only, and is not intended to be limiting.

What is claimed is:

1. A robot comprising:
   a member;
   a joint configured to control motion of the member;
   a motor disposed within a housing at the joint and comprising a rotor;
   a controller comprising one or more printed circuit boards (PCBs) disposed within the housing and a plurality of field-effect transistors (FETs) disposed on a surface of a PCB of the one or more PCBs, the one or more PCBs comprising one or more processors configured to control the motor;
   a first rotary position sensor mounted on the controller;
   a shaft coupled to the rotor of the motor and extending through at least one of the one or more PCBs;
   a magnet mounted within the shaft, the magnet adjacent to and facing the first rotary position sensor; and
   a second rotary position sensor coupled the member of the robot, the second rotary position sensor configured to provide sensor information indicative of a rotary position of the member of the robot.

2. The robot of claim 1, wherein, when the shaft and the magnet rotate, the magnet is diametrically magnetized to enable the first rotary position sensor to capture information indicative of the rotary position of the shaft, the first rotary position sensor communicating with the one or more processors to provide the information indicative of the rotary position of the shaft.

3. The robot of claim 1, wherein the one or more PCBs comprise:
   a power stage PCB configured to control electrical power to the motor; and
   a logic stage PCB configured to control operations for the motor.

4. The robot of claim 3, wherein the plurality of FETs are disposed on a first surface of the power stage PCB facing the motor.

5. The robot of claim 3, wherein the power stage PCB is disposed between the motor and the logic stage PCB.

6. The robot of claim 3, wherein the first rotary position sensor is mounted on a first surface of the logic stage PCB, the logic stage PCB defined by a plane axially spaced from a respective plane of the power stage PCB.

7. The robot of claim 6, wherein:
   the plurality of FETs are disposed on a first surface of the power stage PCB facing the motor, and
   the first surface of the logic stage PCB comprising the first rotary position sensor faces:
   the motor; and
   a second surface of the power stage PCB opposite the first surface of the power stage PCB.

8. The robot of claim 1, further comprising a thermal sensor mounted on the surface of the PCB of the one or more PCBs.

9. The robot of claim 1, further comprising a thermally conductive structure protruding from an interior peripheral surface of the housing, the thermally conductive structure separated by a thermal interfacial material from the surface of the PCB of the one or more PCBs that includes the plurality of FETs are mounted, the thermal interfacial material in contact with and configured to promote thermal contact conductance between the thermally conductive structure and the surface of the PCB of the one or more PCBs that includes the plurality of FETs.

10. The robot of claim 9, wherein the thermally conductive structure comprises ribs forming a heat dissipation path, the heat dissipation path configured to dissipate heat generated by the motor.

11. An assembly comprising:
    a housing at a joint of a robot, the joint configured to control motion of a member of the robot, the housing having an interior surface comprising a thermally conductive structure protruding inwards towards an interior cavity of the housing;
    a motor disposed within the interior cavity of the housing and comprising a stator and a rotor, the rotor coupled to a shaft, the shaft comprising a magnet at a first end of the shaft opposite a second end of the shaft, the second end of the shaft coupled to a transmission of the motor;
    a controller disposed within the interior cavity of the housing and comprising one or more printed circuit boards (PCBs), the one or more PCBs comprising a plurality of field-effect transistors (FETs) and at least one rotary position sensor; and
    a thermal interfacial material in contact with a portion of the controller and the motor, the thermal interfacial material configured to dissipate heat from the controller and the motor to the thermally conductive structure of the housing.

12. The assembly of claim 11, wherein, when the shaft and the magnet rotate, the magnet is diametrically magnetized to enable a first rotary position sensor of the at least one rotary position sensor to capture information indicative of the rotary position of the shaft, the first rotary position sensor providing the information indicative of the rotary position of the shaft to the controller.

13. The assembly of claim 11, wherein the one or more PCBs comprise:
    a power stage PCB configured to control electrical power to the motor; and
    a logic stage PCB configured to control operations for the motor.

14. The assembly of claim 13, wherein the plurality of FETs are disposed on a first surface of the power stage PCB facing the motor.

15. The assembly of claim 13, wherein the power stage PCB is disposed between the motor and the logic stage PCB.

16. The assembly of claim 13, wherein the at least one rotary position sensor comprises a first rotary position sensor mounted on a first surface of the logic stage PCB, the logic stage PCB defined by a plane axially spaced from a respective plane of the power stage PCB.

17. The assembly of claim 16, wherein:
the plurality FETs are disposed on a first surface of the power stage PCB facing the motor, and
the first surface of the logic stage PCB comprising the first rotary position sensor faces:
the motor; and
a second surface of the power stage PCB opposite the first surface of the power stage PCB.

18. The assembly of claim 11, further comprising a thermal sensor mounted on a surface of a respective PCB of the one or more PCBs, the respective PCB comprising the plurality of FETs.

19. The assembly of claim 11, wherein the thermally interfacial material separates the thermal interfacial material from a respective PCB of the one or more PCBs that includes the plurality of FETs, the thermal interfacial material in contact with and configured to promote thermal contact conductance between the thermally conductive structure and the respective PCB of the one or more PCBs that includes the plurality of FETs.

20. The assembly of claim 19, wherein the thermally conductive structure comprises ribs configured to dissipate heat generated by the motor.

21. The assembly of claim 11, wherein the controller further comprises one or more processors and data storage, the data storage comprising instructions executable by the one or more processors to perform operations, the operations comprising:
receiving information indicative of a rotary position of the shaft of the motor from a first rotary position sensor of the at least one rotary position sensor;
receiving, from a second rotary position sensor of the at least one rotary position sensor, measurements indicative of a respective rotary position that defines movement of the member about the joint of the robot; and
determining that rotary motion of the shaft of the motor results in a transmission slip for the transmission corresponding to the motor based on the received information indicative of the rotary position of the shaft of the motor and the received measurements indicative of the respective rotary position that defines movement of the member about the joint of the robot.

22. The assembly of claim 21, wherein the operations further comprise measuring a torque load on the transmission, the torque load measured by a torque sensor.

23. The assembly of claim 22, wherein the operations further comprise processing, by a flexible PCB of the controller, signals from at least one of the torque sensor or the second rotary position sensor.

* * * * *